US009387308B2

(12) United States Patent
Hinchliffe et al.

(10) Patent No.: US 9,387,308 B2
(45) Date of Patent: Jul. 12, 2016

(54) GUIDEWIRE WITH ADJUSTABLE STIFFNESS

(75) Inventors: Peter W. J. Hinchliffe, Campbell Hall, NY (US); Joseph Martin Freeley, Balhaunis (IE); Cormac Flynn, Shannon (IE); Ivan Mooney, Taum (IE); Henry Lupton, Oranmore (IE); Juan Carlos Parodi, Pcia (AR)

(73) Assignee: CARDIOGUIDANCE BIOMEDICAL, LLC, Arlington, VA (US)

( * ) Notice: Subject to any disclaimer, the term of this patent is extended or adjusted under 35 U.S.C. 154(b) by 1304 days.

(21) Appl. No.: 12/660,891

(22) Filed: Mar. 5, 2010

(65) Prior Publication Data

US 2010/0305475 A1 Dec. 2, 2010

Related U.S. Application Data

(63) Continuation-in-part of application No. 12/082,507, filed on Apr. 11, 2008, now abandoned.

(60) Provisional application No. 60/913,489, filed on Apr. 23, 2007, provisional application No. 61/008,100, filed on Dec. 17, 2007, provisional application No. 61/159,178, filed on Mar. 11, 2009, provisional application No. 61/257,483, filed on Nov. 3, 2009.

(51) Int. Cl.
*A61M 25/09* (2006.01)
*A61M 25/00* (2006.01)

(52) U.S. Cl.
CPC ......... *A61M 25/09041* (2013.01); *A61M 25/09* (2013.01); *A61M 25/0905* (2013.01); *A61M 25/09025* (2013.01); *A61M 2025/0006* (2013.01); *A61M 2025/0042* (2013.01); *A61M 2025/0915* (2013.01); *A61M 2025/09075* (2013.01); *A61M 2025/09083* (2013.01); *A61M 2025/09091* (2013.01); *A61M 2025/09116* (2013.01); *A61M 2025/09133* (2013.01); *A61M 2025/09175* (2013.01)

(58) Field of Classification Search
CPC ................ A61M 25/01; A61M 25/09; A61M 25/09016; A61M 25/09025; A61M 25/09033; A61M 25/09041; A61M 25/0905
USPC ........................................... 600/585; 604/510
See application file for complete search history.

(56) References Cited

U.S. PATENT DOCUMENTS 3,633,579 A  1/1972  Alley
4,215,703 A  8/1980  Willson
(Continued)

FOREIGN PATENT DOCUMENTS

DE  10017147  10/2001
EP  0597341  5/1994
(Continued)

*Primary Examiner* — Michael C Stout

(57) ABSTRACT

A medical guidewire system including an inner member having an outer diameter and an outer member having an inner diameter, the inner diameter being larger than the outer diameter. The inner and outer members are relatively slidable to adjust a stiffness of the guidewire system. The lumen of the outer member forms a gap for fluid flow therethrough. A connector has a first end portion connected to the outer member, a second end portion connected to the inner member and a fluid infusion channel communicating with the gap for injection of fluid through the gap to exit a distal portion of the outer member.

19 Claims, 18 Drawing Sheets

(56) References Cited

U.S. PATENT DOCUMENTS

| | | | |
|---|---|---|---|
| 4,548,206 A | 10/1985 | Osborne | |
| 4,616,652 A * | 10/1986 | Simpson | A61M 25/104 600/434 |
| 4,676,249 A | 6/1987 | Arenas et al. | |
| 4,779,628 A | 10/1988 | Machek | |
| 4,781,703 A | 11/1988 | Walker et al. | |
| 4,822,345 A | 4/1989 | Danforth | |
| 4,827,941 A | 5/1989 | Taylor et al. | |
| 4,834,702 A * | 5/1989 | Rocco | A61B 17/22 251/4 |
| 4,834,709 A | 5/1989 | Banning et al. | |
| 4,846,193 A | 7/1989 | Tremulis et al. | |
| 4,873,983 A | 10/1989 | Winters | |
| 4,874,376 A * | 10/1989 | Hawkins, Jr. | A61M 25/065 600/585 |
| 4,875,489 A | 10/1989 | Messner et al. | |
| 4,895,168 A | 1/1990 | Machek | |
| 4,932,413 A | 6/1990 | Shockey et al. | |
| 4,947,864 A | 8/1990 | Shockey | |
| 4,966,163 A | 10/1990 | Kraus et al. | |
| 5,040,543 A | 8/1991 | Badera et al. | |
| 5,059,183 A * | 10/1991 | Semrad | A61M 25/06 600/585 |
| 5,095,915 A | 3/1992 | Engelson | |
| 5,109,867 A | 5/1992 | Twyford, Jr. | |
| 5,178,159 A | 1/1993 | Christian | |
| 5,184,627 A | 2/1993 | de Toledo | |
| 5,207,229 A | 5/1993 | Winters | |
| 5,224,939 A | 7/1993 | Holman et al. | |
| 5,234,002 A | 8/1993 | Chan | |
| 5,246,009 A | 9/1993 | Adams | |
| 5,269,793 A | 12/1993 | Simpson | |
| 5,271,415 A | 12/1993 | Foerster et al. | |
| 5,281,203 A | 1/1994 | Ressemann | |
| 5,304,131 A | 4/1994 | Paskar | |
| 5,307,808 A * | 5/1994 | Dumoulin | G01R 33/285 600/420 |
| 5,312,338 A | 5/1994 | Nelson et al. | |
| 5,315,996 A | 5/1994 | Lundquist | |
| 5,334,168 A | 8/1994 | Hemmer | |
| 5,341,817 A | 8/1994 | Viera | |
| 5,363,861 A | 11/1994 | Edwards et al. | |
| 5,365,943 A | 11/1994 | Jansen | |
| 5,372,144 A | 12/1994 | Mortier et al. | |
| 5,385,152 A * | 1/1995 | Abele | A61B 17/22 600/434 |
| 5,387,193 A * | 2/1995 | Miraki | A61M 25/104 604/102.02 |
| 5,419,340 A * | 5/1995 | Stevens | A61M 25/0102 600/434 |
| 5,421,348 A | 6/1995 | Larnard | |
| 5,437,288 A | 8/1995 | Schwartz et al. | |
| 5,484,424 A | 1/1996 | Cottenceau et al. | |
| 5,527,298 A | 6/1996 | Vance et al. | |
| 5,546,958 A | 8/1996 | Thorud et al. | |
| 5,551,444 A | 9/1996 | Finlayson | |
| 5,558,635 A | 9/1996 | Cannon | |
| 5,605,162 A | 2/1997 | Mirzaee et al. | |
| 5,693,015 A | 12/1997 | Walker | |
| 5,695,483 A * | 12/1997 | Samson | A61L 29/041 600/585 |
| 5,716,389 A * | 2/1998 | Walinsky | A61B 5/0422 600/374 |
| 5,741,429 A * | 4/1998 | Donadio, III | A61M 25/0043 216/10 |
| 5,746,701 A | 5/1998 | Noone | |
| 5,792,075 A | 8/1998 | Schwager | |
| 5,807,330 A | 9/1998 | Teitelbaum | |
| 5,807,339 A * | 9/1998 | Bostrom | A61M 25/0041 604/164.01 |
| 5,810,012 A | 9/1998 | Lynch | |
| 5,810,867 A | 9/1998 | Zarbatany et al. | |
| 5,813,405 A * | 9/1998 | Montano, Jr. | A61M 25/0905 600/585 |
| 5,827,201 A | 10/1998 | Samson et al. | |
| 5,833,632 A * | 11/1998 | Jacobsen | A61M 25/09 600/373 |
| 5,836,893 A * | 11/1998 | Urick | A61M 25/09 600/433 |
| 5,931,842 A * | 8/1999 | Goldsteen | A61B 1/0058 606/108 |
| 5,938,623 A | 8/1999 | Quiachon et al. | |
| 5,957,903 A | 9/1999 | Mirzaee | |
| 5,998,742 A * | 12/1999 | Liu | G01G 7/02 177/184 |
| 6,001,068 A | 12/1999 | Uchino et al. | |
| 6,004,279 A * | 12/1999 | Crowley | A61M 25/09 600/433 |
| 6,024,730 A | 2/2000 | Pagan | |
| RE36,628 E * | 3/2000 | Sagae | A61M 25/09 148/537 |
| 6,059,748 A * | 5/2000 | Teirstein | A61M 25/0169 604/158 |
| 6,080,117 A | 6/2000 | Cornelius | |
| 6,095,990 A | 8/2000 | Parodi | |
| 6,113,557 A | 9/2000 | Fagan et al. | |
| 6,123,698 A | 9/2000 | Spears | |
| 6,152,909 A * | 11/2000 | Bagaoisan | A61B 17/22 604/173 |
| 6,165,140 A | 12/2000 | Ferrera | |
| 6,183,420 B1 * | 2/2001 | Douk | A61M 25/09 600/434 |
| 6,190,393 B1 * | 2/2001 | Bevier | A61F 2/958 604/96.01 |
| 6,241,690 B1 | 6/2001 | Burkett et al. | |
| 6,390,993 B1 | 5/2002 | Cornish et al. | |
| 6,394,976 B1 * | 5/2002 | Winston | A61M 25/09041 604/95.04 |
| 6,428,489 B1 | 8/2002 | Jacobsen et al. | |
| 6,432,066 B1 | 8/2002 | Ferrera | |
| 6,461,311 B2 | 10/2002 | DuBois et al. | |
| 6,488,637 B1 | 12/2002 | Eder et al. | |
| 6,500,202 B1 * | 12/2002 | Shaolian | A61F 2/07 623/1.11 |
| 6,503,244 B2 * | 1/2003 | Hayman | A61J 1/2096 604/103.09 |
| 6,524,303 B1 | 2/2003 | Garibaldi | |
| 6,544,197 B2 | 4/2003 | DeMello | |
| 6,544,231 B1 | 4/2003 | Palmer et al. | |
| 6,579,246 B2 | 6/2003 | Jacobsen et al. | |
| 6,579,277 B1 | 6/2003 | Rabiner et al. | |
| 6,579,302 B2 | 6/2003 | Duerig et al. | |
| 6,599,254 B2 | 7/2003 | Winters | |
| 6,623,449 B2 | 9/2003 | Paskar | |
| 6,652,472 B2 | 11/2003 | Jafari et al. | |
| 6,656,152 B2 * | 12/2003 | Putz | A61M 25/0662 604/510 |
| 6,660,030 B2 | 12/2003 | Shaolian et al. | |
| 6,663,577 B2 | 12/2003 | Jen et al. | |
| 6,663,665 B2 | 12/2003 | Shaolian | |
| 6,669,652 B2 | 12/2003 | Anderson et al. | |
| 6,682,493 B2 | 1/2004 | Mirigian | |
| 6,685,653 B2 | 2/2004 | Ehr et al. | |
| 6,755,794 B2 | 6/2004 | Soukup | |
| 6,773,448 B2 | 8/2004 | Kusleika et al. | |
| 6,776,765 B2 | 8/2004 | Soukup et al. | |
| 6,802,835 B2 | 10/2004 | Rabiner et al. | |
| 6,805,675 B1 | 10/2004 | Gardeski et al. | |
| 6,805,676 B2 | 10/2004 | Klint | |
| 6,824,550 B1 | 11/2004 | Noriega et al. | |
| 6,837,870 B2 | 1/2005 | Duchamp | |
| 6,887,229 B1 | 5/2005 | Kurth | |
| 6,911,016 B2 | 6/2005 | Balzum et al. | |
| 6,939,361 B1 | 9/2005 | Kleshinski | |
| 6,986,749 B2 | 1/2006 | Wollschlager | |
| 7,025,734 B1 * | 4/2006 | Ellis | A61B 5/14542 600/345 |
| 7,025,758 B2 | 4/2006 | Klint | |
| 7,097,624 B2 | 8/2006 | Campion et al. | |
| 7,104,979 B2 | 9/2006 | Jansen et al. | |
| 7,115,134 B2 * | 10/2006 | Chambers | A61M 25/0041 604/525 |
| 7,137,654 B2 | 11/2006 | Segal | |
| 7,163,523 B2 | 1/2007 | Devens et al. | |

(56) References Cited

U.S. PATENT DOCUMENTS

| | | | |
|---|---|---|---|
| 7,192,433 B2* | 3/2007 | Osypka | A61M 25/0668 604/164.05 |
| 7,367,967 B2 | 5/2008 | Eidenschink | |
| 7,402,141 B2* | 7/2008 | Heuser | 600/585 |
| 7,494,474 B2 | 2/2009 | Richardson et al. | |
| 7,632,242 B2* | 12/2009 | Griffin | A61B 17/22032 604/102.01 |
| 7,708,704 B2* | 5/2010 | Mitelberg et al. | 600/585 |
| 7,850,623 B2* | 12/2010 | Griffin | A61M 25/0013 600/585 |
| 8,038,628 B2* | 10/2011 | von Malmborg | A61B 5/0215 600/585 |
| 8,439,937 B2* | 5/2013 | Montague et al. | 606/159 |
| 2002/0048310 A1* | 4/2002 | Heuser | A61B 5/01 374/141 |
| 2002/0095174 A1 | 7/2002 | Tsugita | |
| 2003/0040666 A1* | 2/2003 | Rutten | A61B 5/042 600/374 |
| 2003/0040735 A1 | 2/2003 | Kunis et al. | |
| 2003/0060731 A1 | 3/2003 | Fleischhacke | |
| 2003/0060802 A1 | 3/2003 | Omaleki et al. | |
| 2003/0069522 A1 | 4/2003 | Jacobsen et al. | |
| 2003/0139689 A1* | 7/2003 | Shturman | A61M 25/0136 600/585 |
| 2004/0006329 A1* | 1/2004 | Scheu | A61M 25/09041 604/528 |
| 2004/0019359 A1 | 1/2004 | Worley et al. | |
| 2004/0034311 A1 | 2/2004 | Mihalcik | |
| 2004/0044350 A1* | 3/2004 | Martin | A61B 17/0469 606/139 |
| 2004/0054322 A1* | 3/2004 | Vargas | A61M 25/00 604/95.04 |
| 2004/0059257 A1 | 3/2004 | Gaber | |
| 2004/0073141 A1 | 4/2004 | Hartley et al. | |
| 2004/0082906 A1* | 4/2004 | Tallarida | A61B 17/0057 604/43 |
| 2004/0097880 A1* | 5/2004 | Schur | A61M 25/007 604/164.01 |
| 2004/0102719 A1 | 5/2004 | Keith et al. | |
| 2004/0122354 A1* | 6/2004 | Semba | A61B 8/06 604/66 |
| 2004/0143197 A1 | 7/2004 | Soukup et al. | |
| 2004/0167437 A1 | 8/2004 | Sharrow et al. | |
| 2004/0180581 A1* | 9/2004 | von Malmborg | A61B 5/04286 439/669 |
| 2004/0181174 A2 | 9/2004 | Davis et al. | |
| 2004/0193073 A1 | 9/2004 | DeMello et al. | |
| 2005/0027214 A1 | 2/2005 | Murayama et al. | |
| 2005/0027249 A1 | 2/2005 | Reifart et al. | |
| 2005/0038358 A1 | 2/2005 | Furukawa | |
| 2005/0038412 A1 | 2/2005 | Rabiner et al. | |
| 2005/0065456 A1 | 3/2005 | Eskuri | |
| 2005/0080400 A1 | 4/2005 | Corcoran et al. | |
| 2005/0085746 A1 | 4/2005 | Adams et al. | |
| 2005/0119590 A1 | 6/2005 | Burmeister et al. | |
| 2005/0124918 A1 | 6/2005 | Griffin et al. | |
| 2005/0137501 A1 | 6/2005 | Euteneuer et al. | |
| 2005/0177132 A1 | 8/2005 | Lentz et al. | |
| 2005/0209631 A1 | 9/2005 | Galdonik et al. | |
| 2005/0273074 A1 | 12/2005 | Lewis | |
| 2005/0288579 A1 | 12/2005 | Miller | |
| 2006/0004346 A1 | 1/2006 | Begg | |
| 2006/0041245 A1* | 2/2006 | Ferry | A61B 1/00133 604/510 |
| 2006/0047222 A1* | 3/2006 | Heuser | A61M 25/01 600/585 |
| 2006/0074398 A1* | 4/2006 | Whiting | A61M 25/0041 604/510 |
| 2006/0074442 A1* | 4/2006 | Noriega | A61B 17/3002 606/159 |
| 2006/0079787 A1* | 4/2006 | Whiting | A61M 25/0041 600/466 |
| 2006/0089569 A1 | 4/2006 | Soukup et al. | |
| 2006/0095015 A1* | 5/2006 | Hobbs | A61B 18/245 604/508 |
| 2006/0100687 A1 | 5/2006 | Fahey et al. | |
| 2006/0121218 A1* | 6/2006 | Obara | A61L 29/085 428/34.7 |
| 2006/0129130 A1 | 6/2006 | Tal et al. | |
| 2006/0184105 A1 | 8/2006 | Townsend et al. | |
| 2006/0189896 A1* | 8/2006 | Davis et al. | 600/585 |
| 2006/0200047 A1* | 9/2006 | Galdonik | A61M 25/0138 600/585 |
| 2006/0241505 A1 | 10/2006 | Ahmed et al. | |
| 2006/0282110 A1* | 12/2006 | Litvack | A61F 2/958 606/192 |
| 2006/0293612 A1 | 12/2006 | Jenson et al. | |
| 2007/0021686 A1* | 1/2007 | Gellman | A61B 17/00234 600/585 |
| 2007/0021821 A1 | 1/2007 | Johnson | |
| 2007/0032779 A1* | 2/2007 | Accisano, III | A61M 25/007 604/541 |
| 2007/0050006 A1* | 3/2007 | Lavelle | A61M 27/008 623/1.11 |
| 2007/0060880 A1 | 3/2007 | Gregorich et al. | |
| 2007/0060914 A1* | 3/2007 | Magnusson | A61M 25/04 604/544 |
| 2007/0083189 A1* | 4/2007 | Lampropoulos | A61M 25/0097 604/541 |
| 2007/0083226 A1 | 4/2007 | Buiser et al. | |
| 2007/0088230 A1* | 4/2007 | Terashi | A61B 17/3207 600/585 |
| 2007/0106245 A1* | 5/2007 | McQueen | A61M 25/09 604/508 |
| 2007/0112302 A1* | 5/2007 | Yu | A61M 25/0606 604/164.01 |
| 2007/0123805 A1* | 5/2007 | Shireman | A61M 25/09 600/585 |
| 2007/0123826 A1 | 5/2007 | Opie et al. | |
| 2007/0135733 A1* | 6/2007 | Soukup | A61M 25/0136 600/585 |
| 2007/0167665 A1* | 7/2007 | Hermann | A61N 5/1015 600/3 |
| 2007/0167876 A1 | 7/2007 | Euteneuer et al. | |
| 2007/0185415 A1 | 8/2007 | Ressemann et al. | |
| 2007/0191765 A1 | 8/2007 | Olsen et al. | |
| 2007/0239141 A1* | 10/2007 | Hartley | A61B 17/221 606/1 |
| 2007/0260225 A1 | 11/2007 | Sakakine et al. | |
| 2007/0287955 A1 | 12/2007 | Layman et al. | |
| 2007/0299502 A1* | 12/2007 | Hebert et al. | 623/1.11 |
| 2008/0015508 A1* | 1/2008 | Hardin, Jr. | A61B 1/015 604/164.13 |
| 2008/0021348 A1 | 1/2008 | Jacobsen et al. | |
| 2008/0027266 A1* | 1/2008 | Lebovic et al. | 600/3 |
| 2008/0051676 A1 | 2/2008 | Melsheimer | |
| 2008/0071279 A1 | 3/2008 | Bandeira et al. | |
| 2008/0097394 A1* | 4/2008 | Lampropoulos | A61M 25/0147 604/524 |
| 2008/0097398 A1* | 4/2008 | Mitelberg | A61M 25/0043 604/525 |
| 2008/0108911 A1* | 5/2008 | Palmer | A61M 25/09041 600/585 |
| 2008/0154153 A1* | 6/2008 | Heuser | A61M 25/01 600/585 |
| 2008/0154207 A1* | 6/2008 | Hardin | A61M 25/09 604/164.13 |
| 2008/0200839 A1 | 8/2008 | Bunch et al. | |
| 2008/0228145 A1* | 9/2008 | Watson | A61M 25/09041 604/164.13 |
| 2008/0312671 A1* | 12/2008 | Riles | A61B 17/32037 606/159 |
| 2008/0319462 A1* | 12/2008 | Montague | A61B 17/320758 606/159 |
| 2009/0012429 A1* | 1/2009 | Heuser | A61M 25/09 600/585 |
| 2009/0099549 A1* | 4/2009 | Miller | A61M 25/0662 604/524 |

(56) References Cited

U.S. PATENT DOCUMENTS

| | | | |
|---|---|---|---|
| 2009/0125045 A1* | 5/2009 | Heuser | A61B 18/1492 606/159 |
| 2009/0216064 A1* | 8/2009 | Lebovic et al. | 600/7 |
| 2010/0004730 A1* | 1/2010 | Benjamin | A61F 2/95 623/1.11 |
| 2010/0087780 A1* | 4/2010 | Tekulve | A61M 25/09025 604/95.01 |
| 2011/0160680 A1* | 6/2011 | Cage | A61M 25/09033 604/265 |

FOREIGN PATENT DOCUMENTS

| | | |
|---|---|---|
| EP | 0773037 | 5/1997 |
| EP | 0778040 | 6/1997 |
| WO | WO 9743949 | 11/1997 |

* cited by examiner

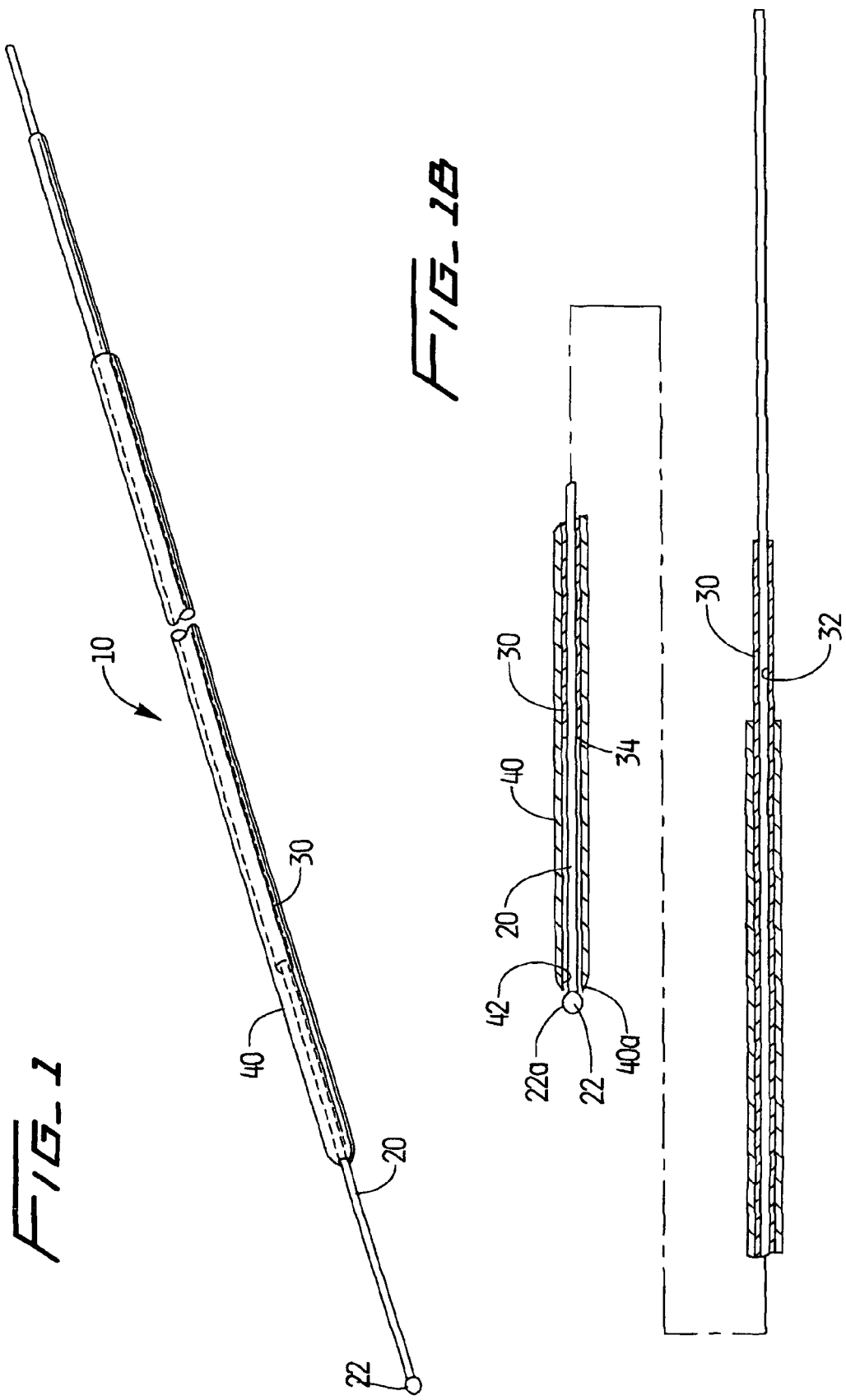

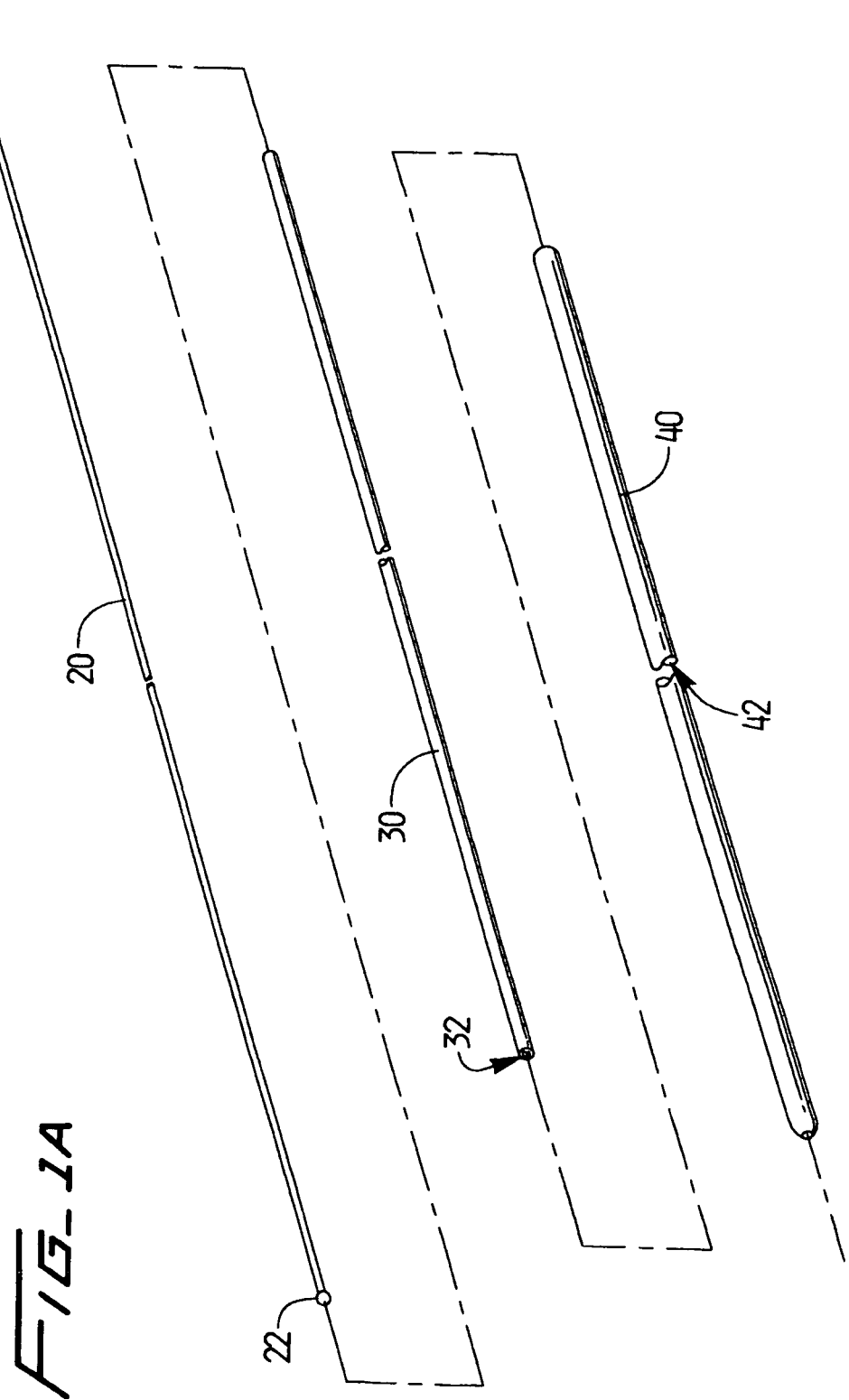

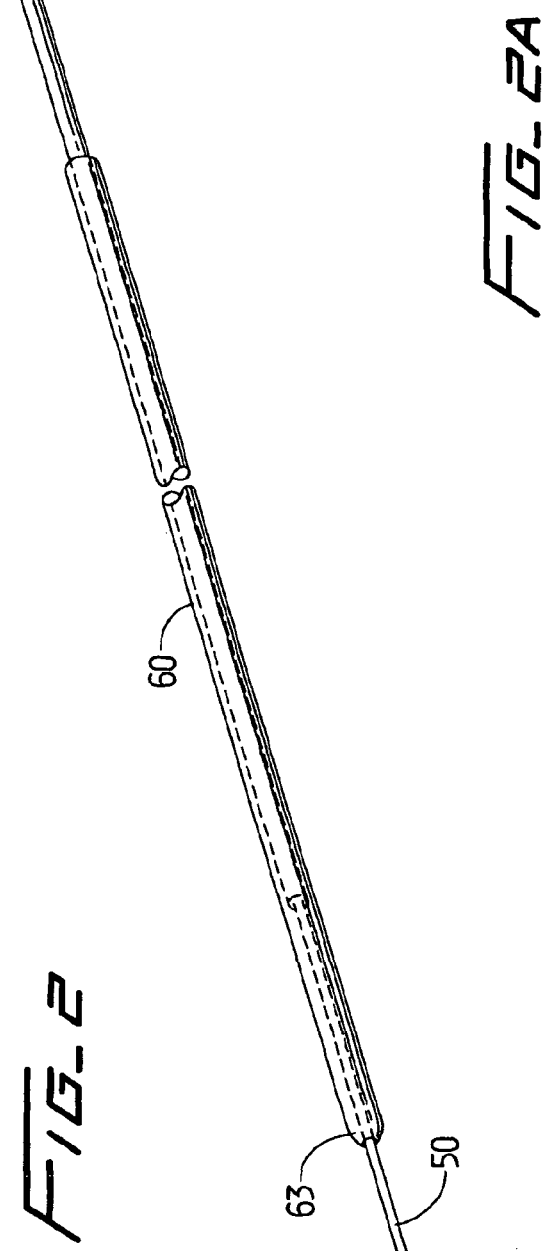
FIG._2
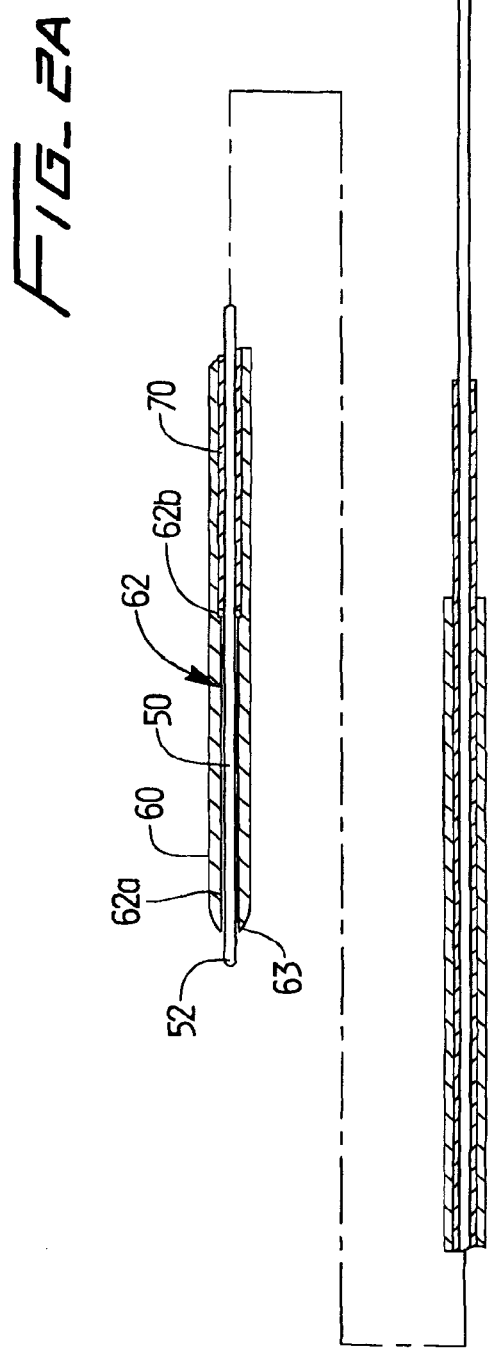
FIG._2A

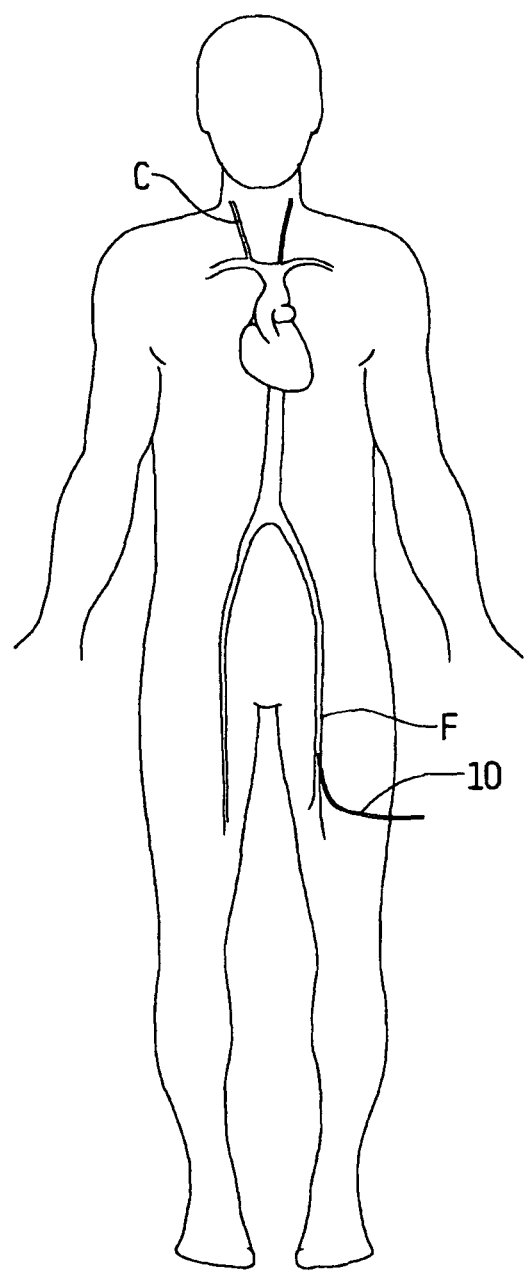

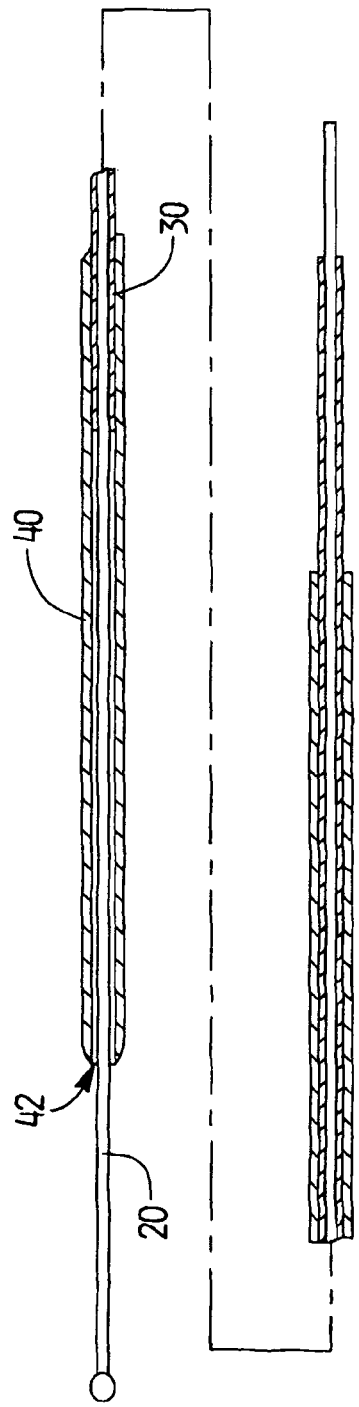
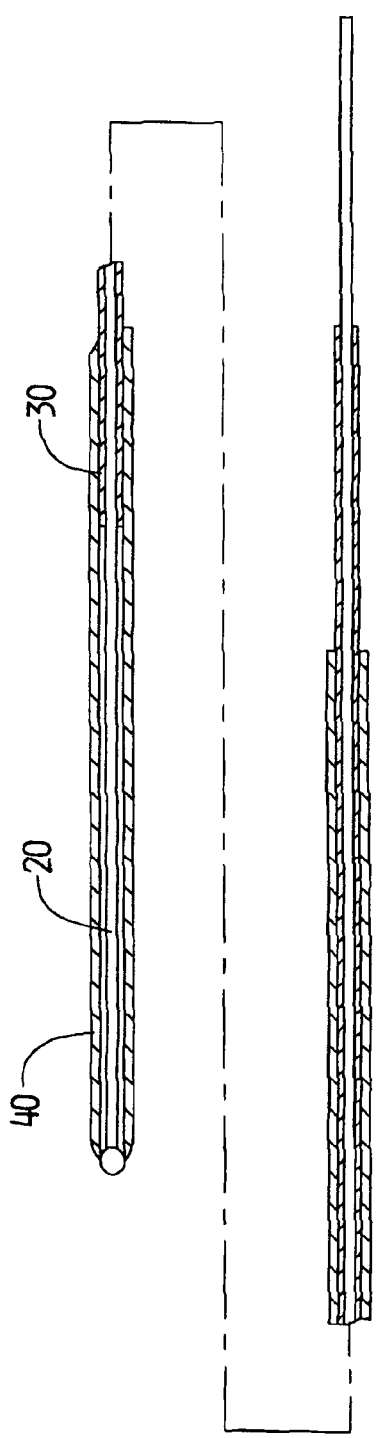

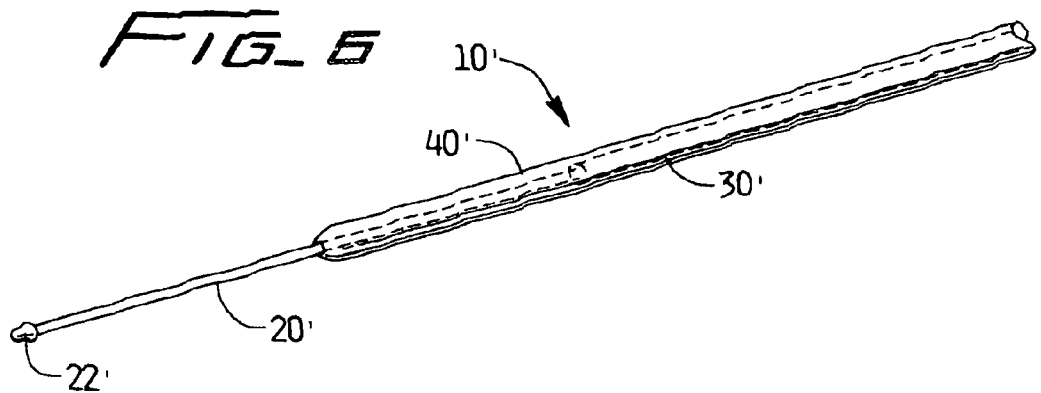
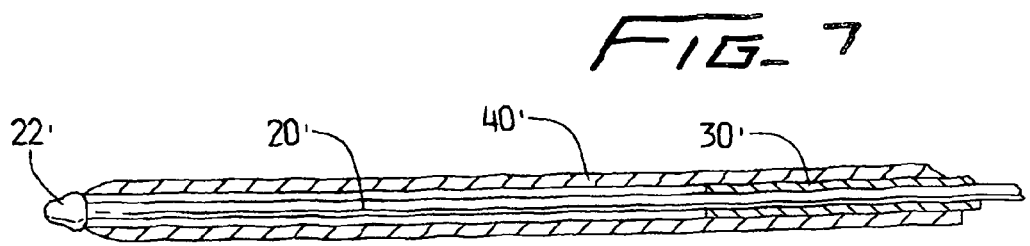
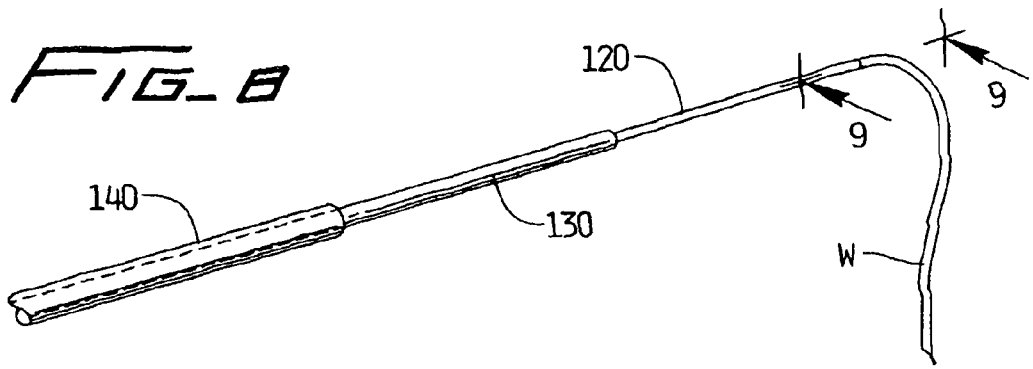
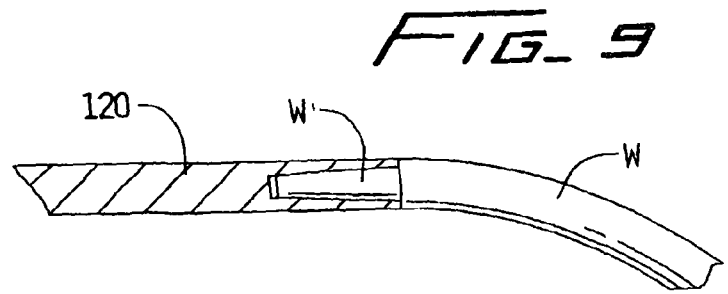

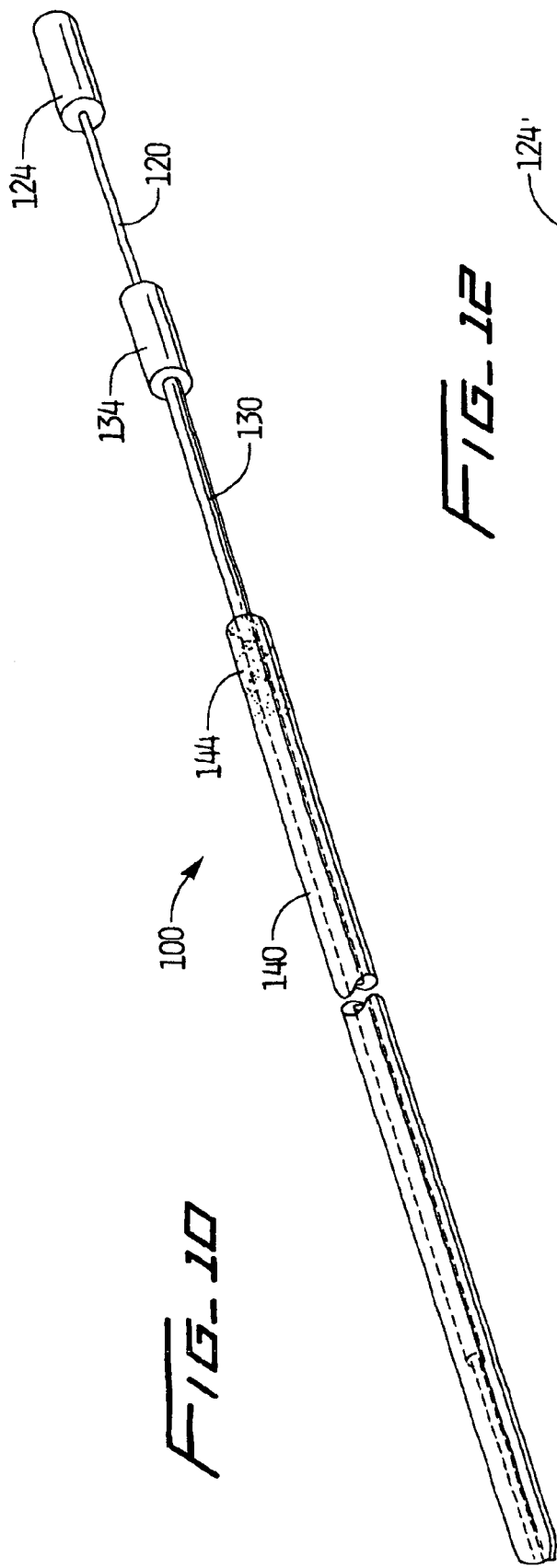
FIG._10
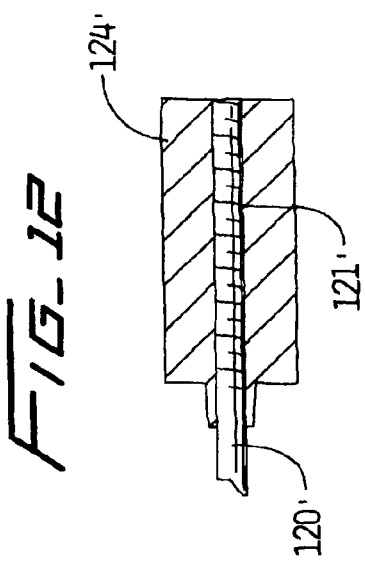
FIG._12
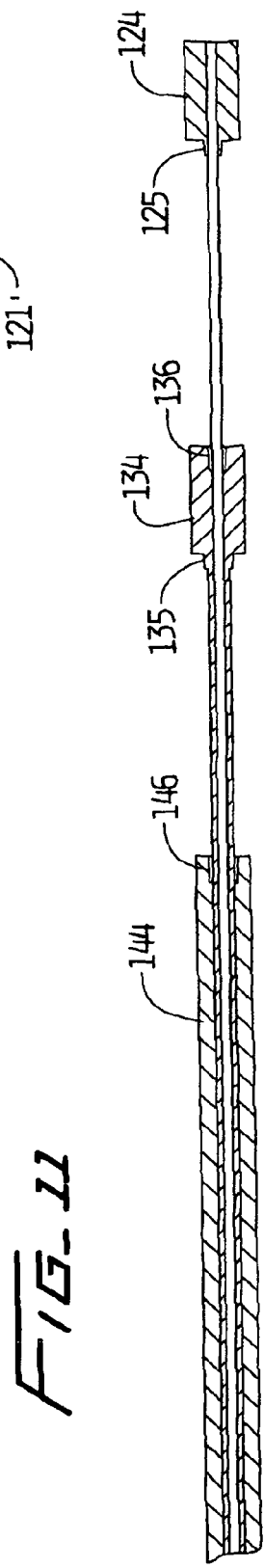
FIG._11

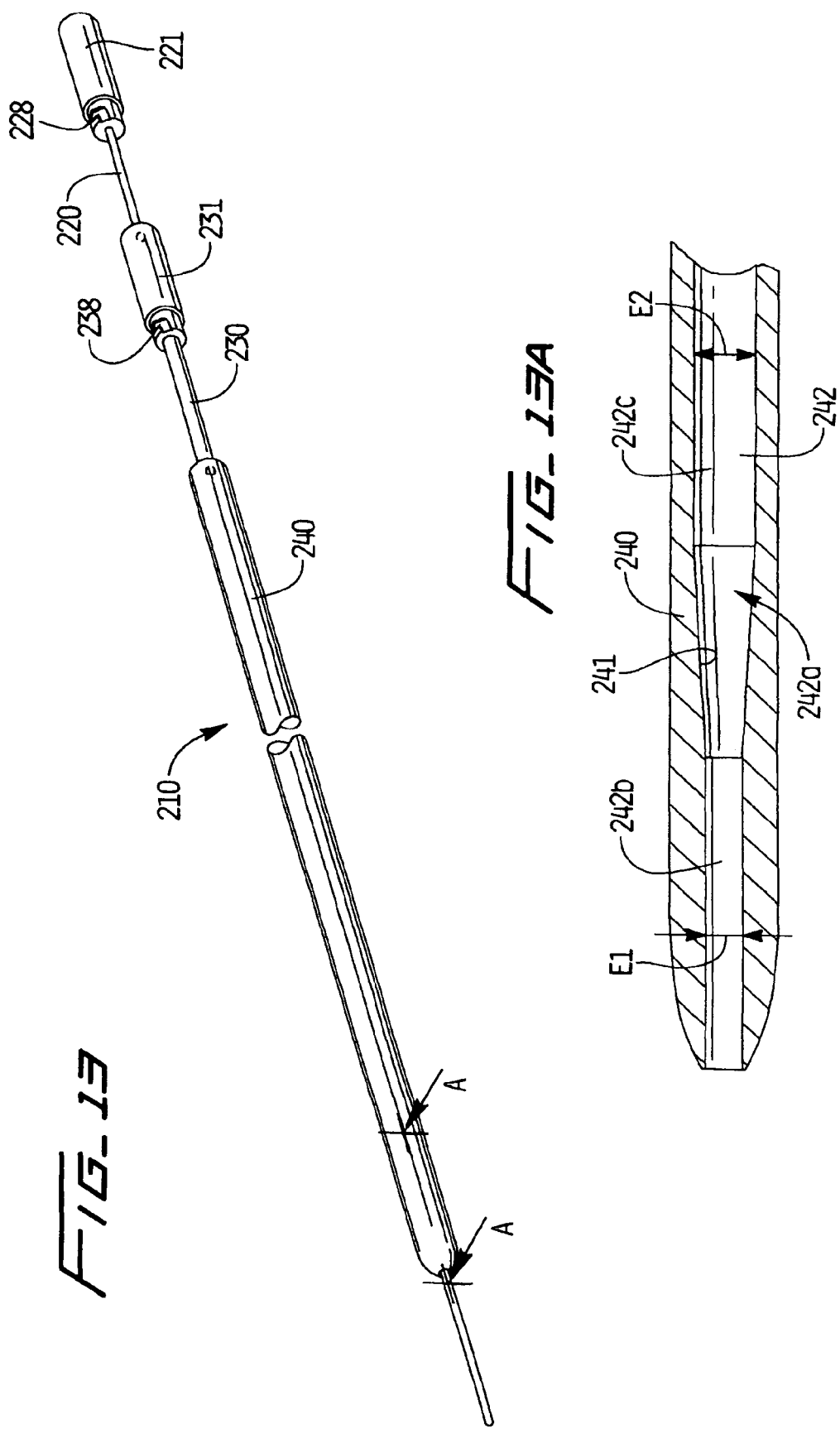

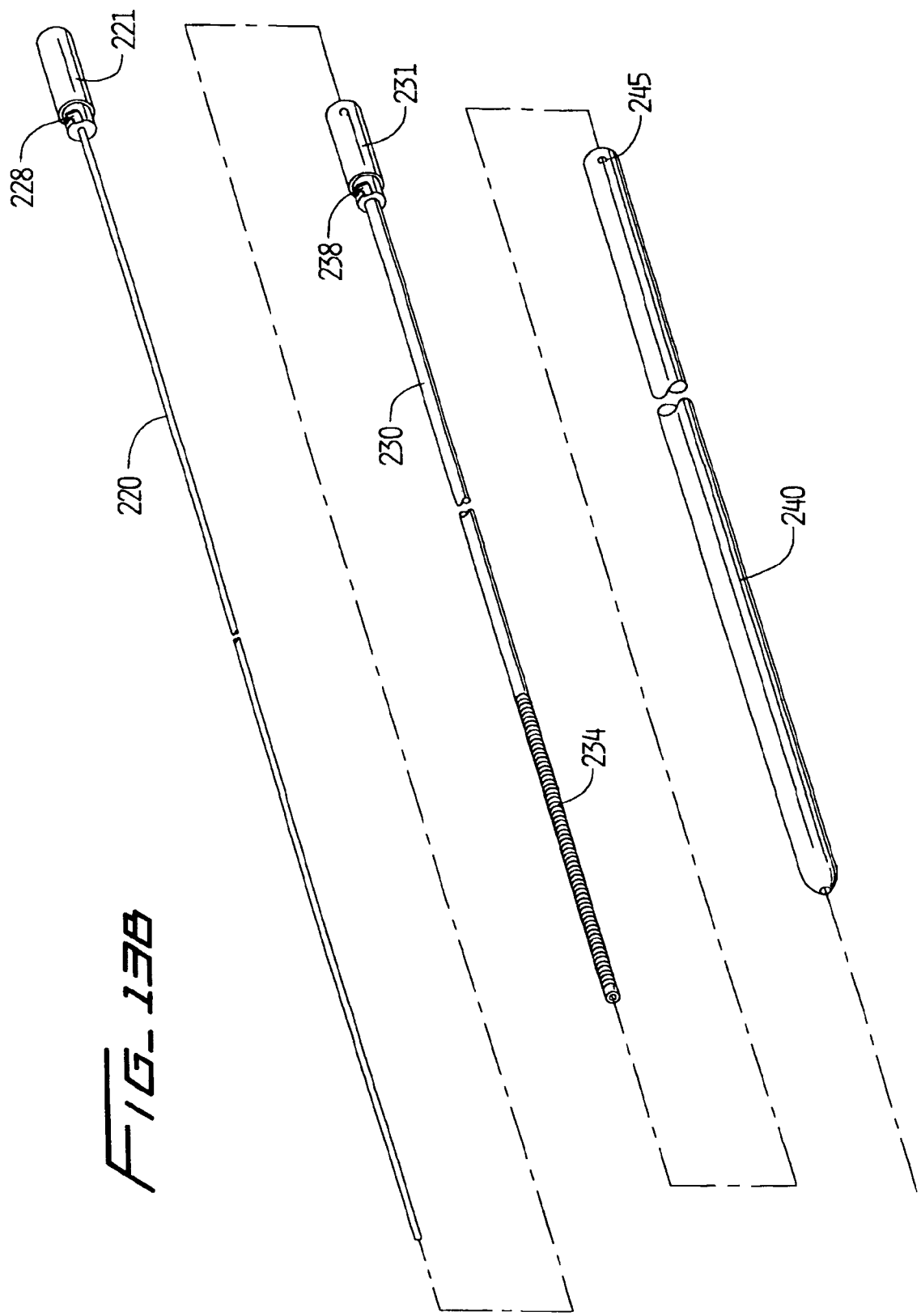

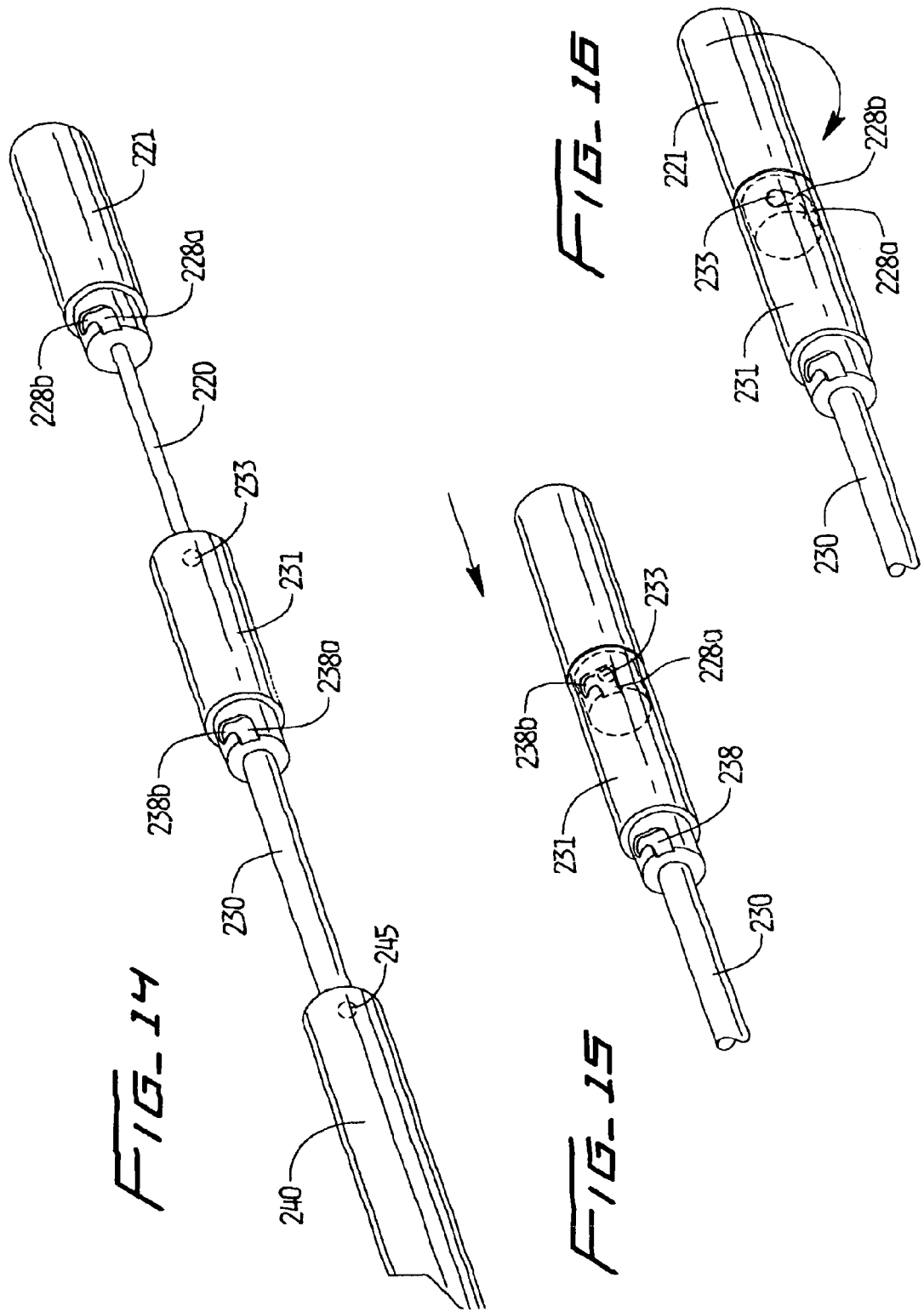

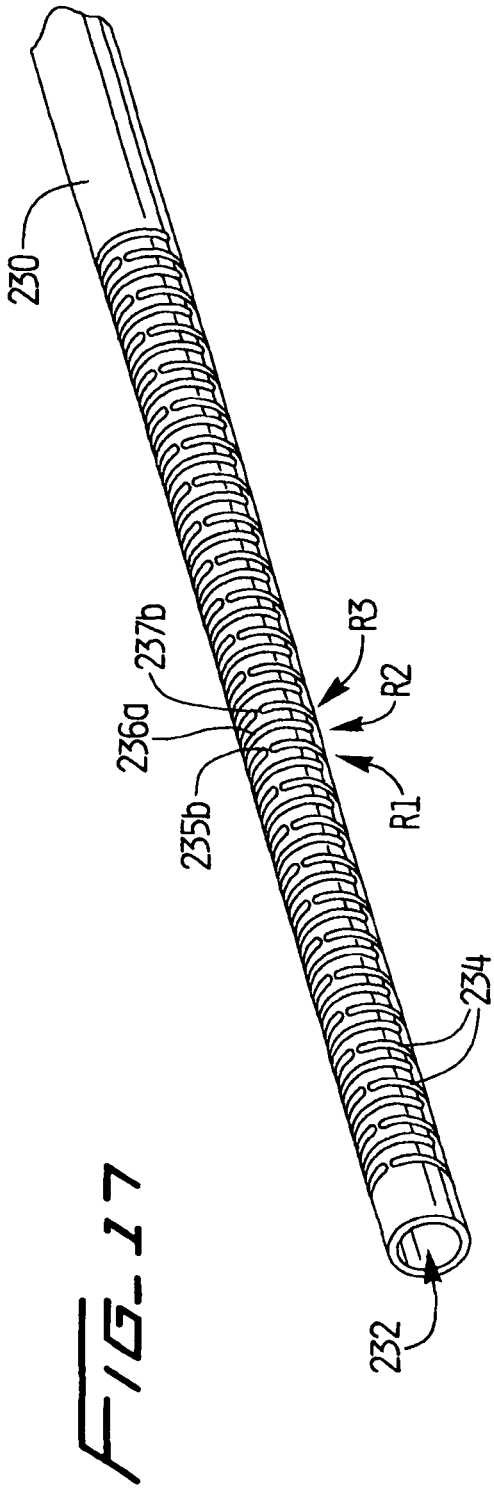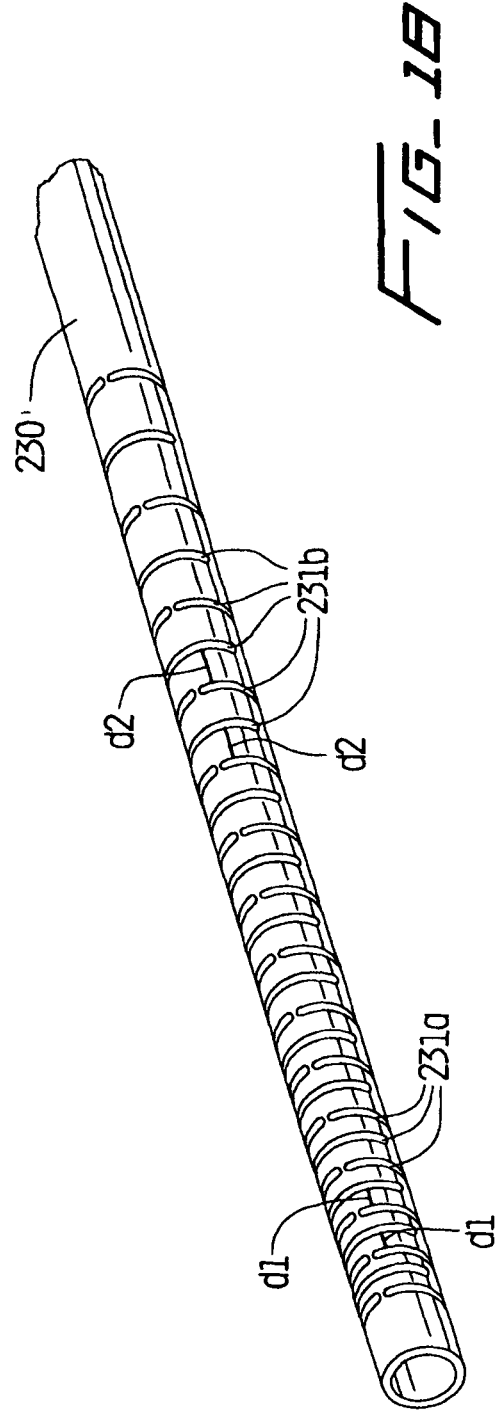

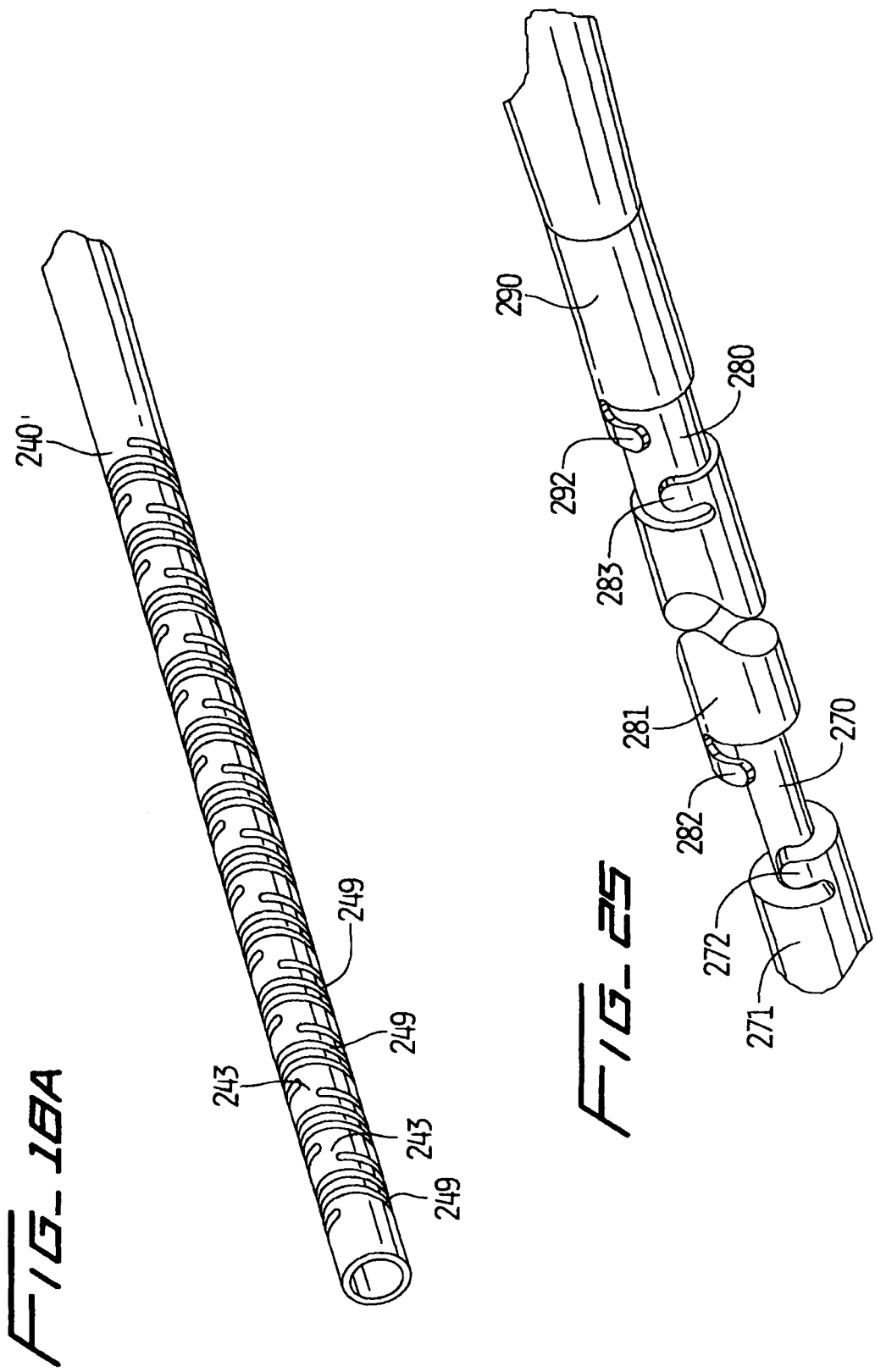

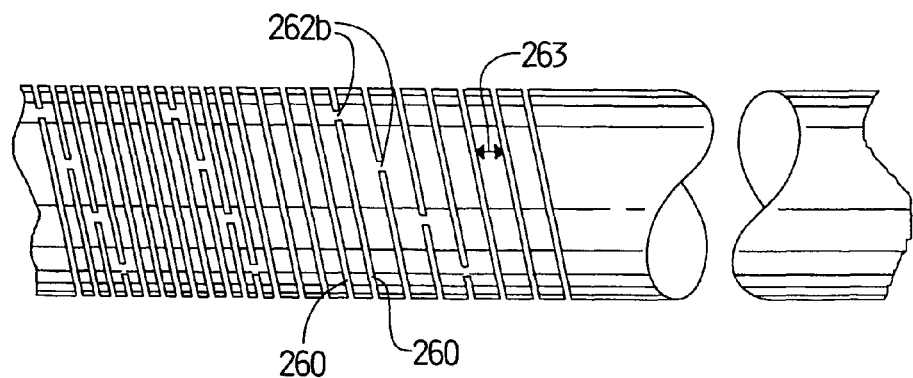
FIG_18B
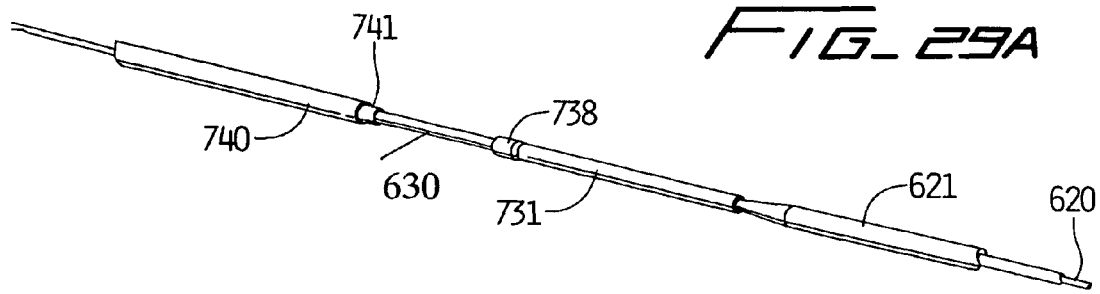
FIG_29A
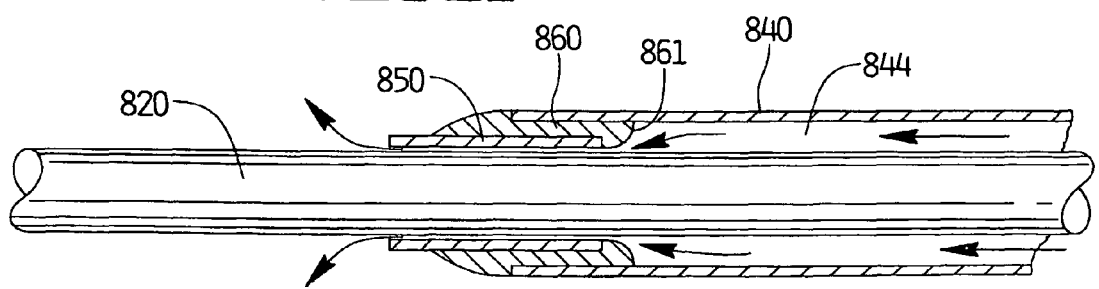
FIG_31

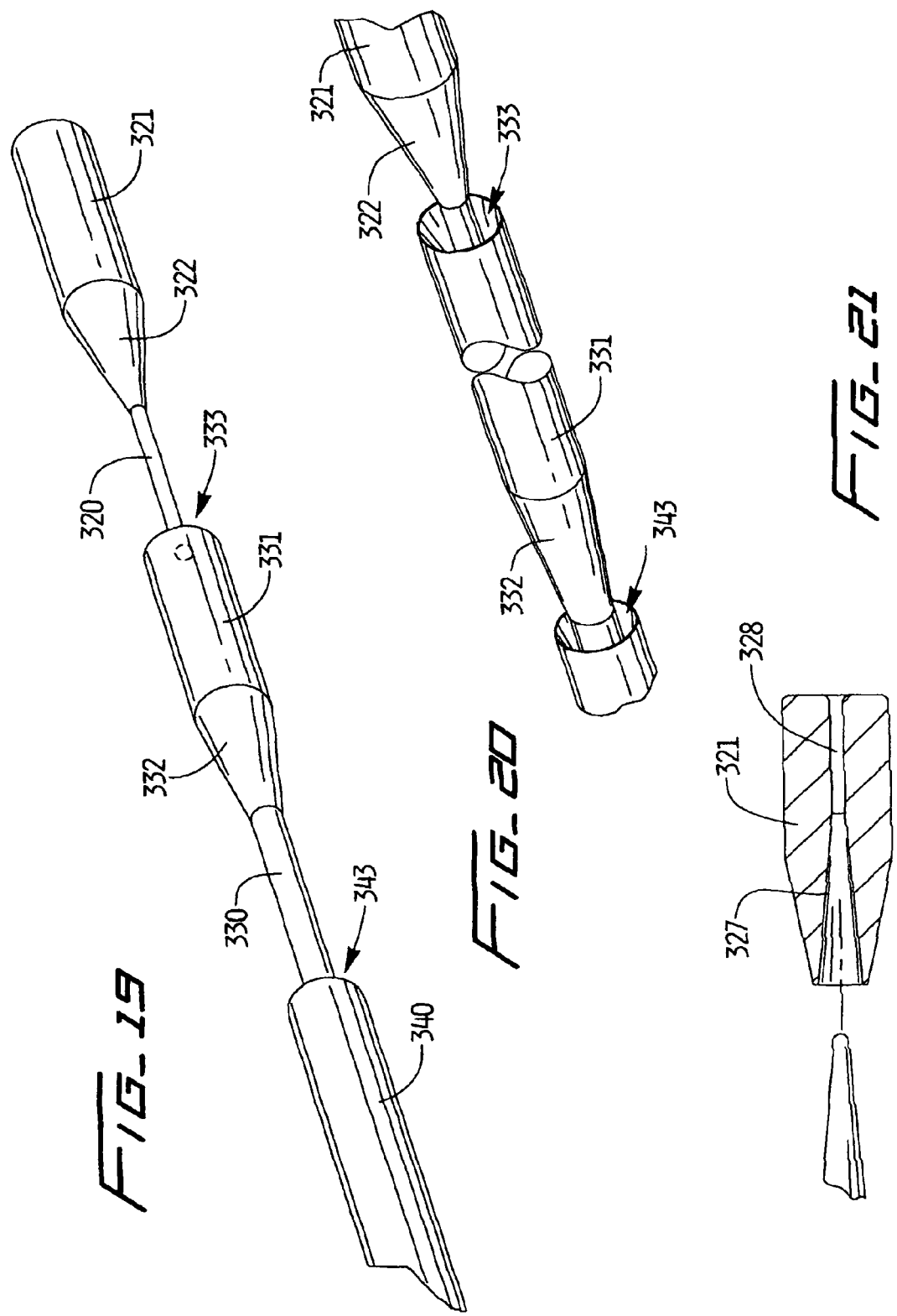

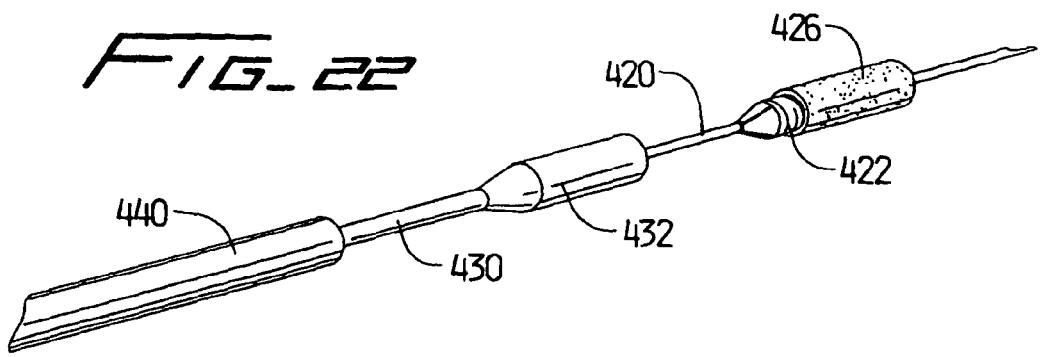
FIG_22
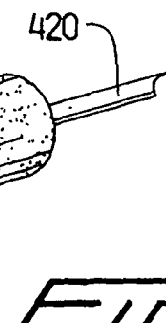
FIG_22A
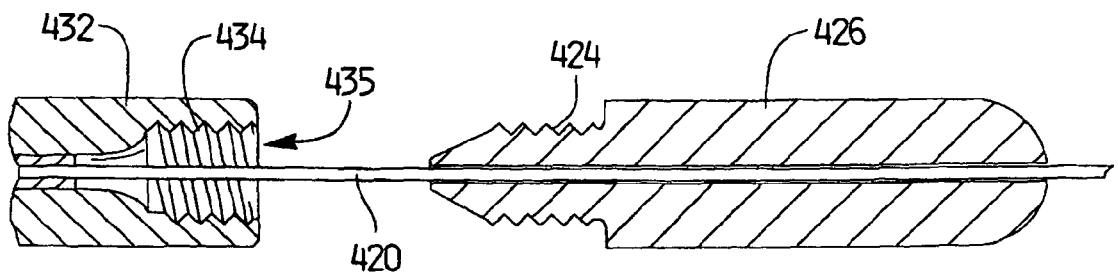
FIG_23
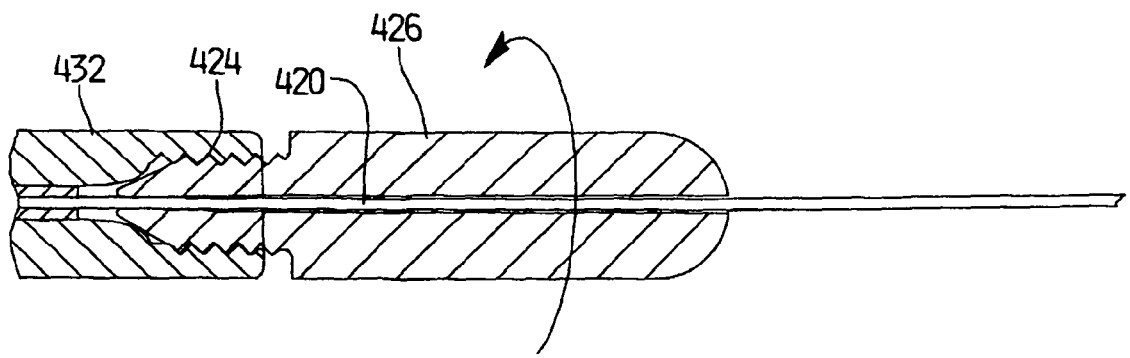
FIG_24

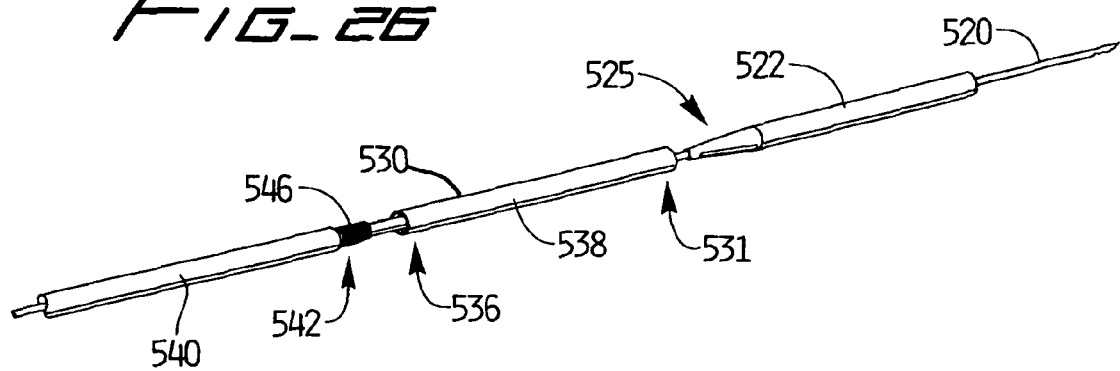
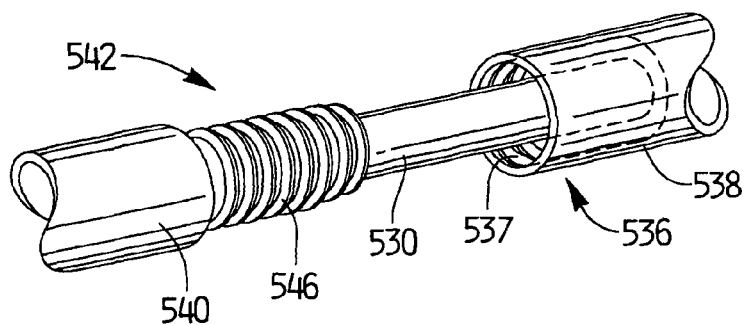
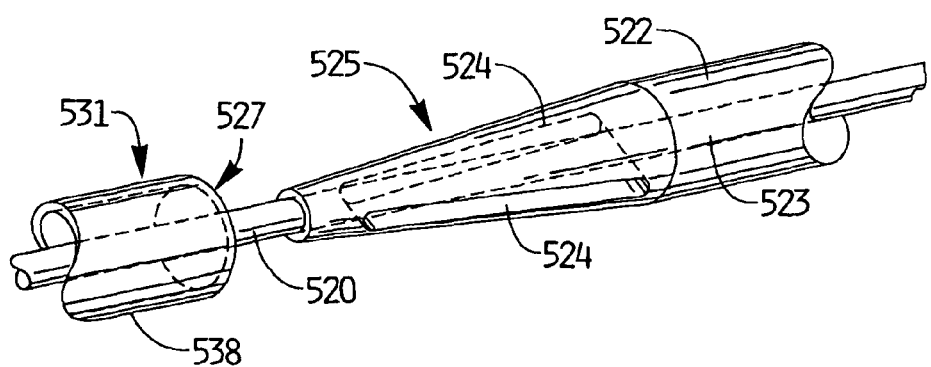

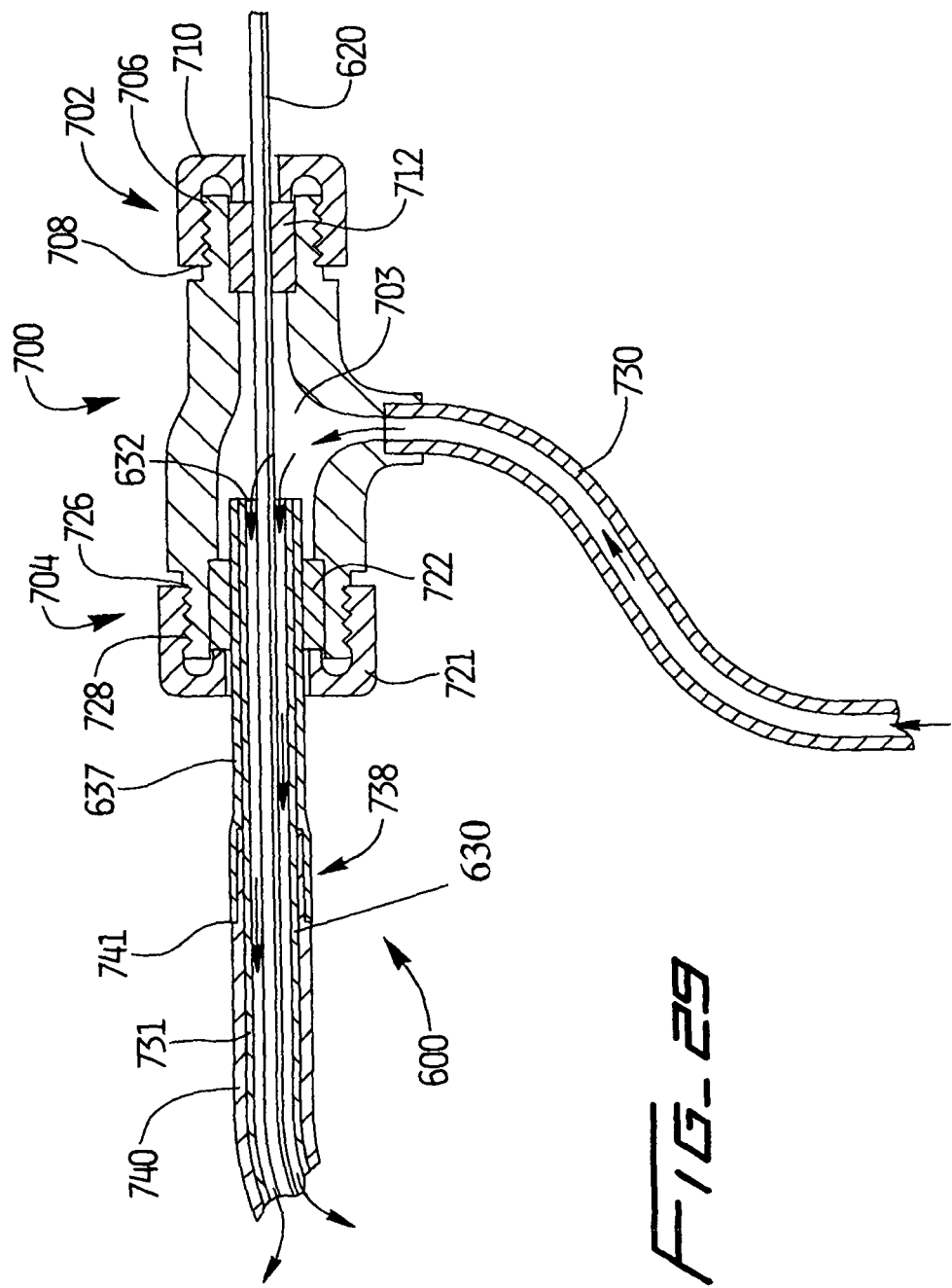

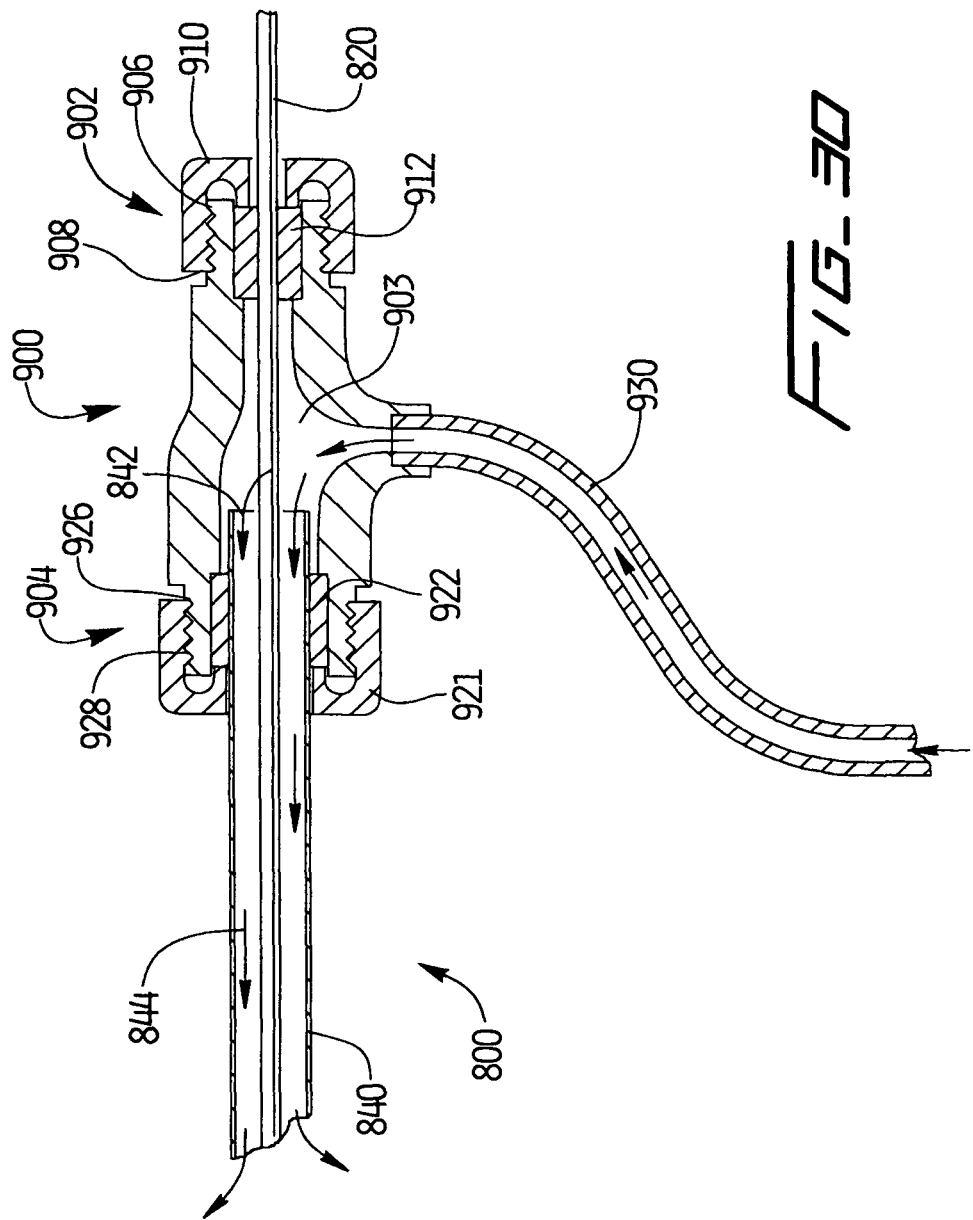

GUIDEWIRE WITH ADJUSTABLE STIFFNESS

This application claims priority from provisional patent application 61/159,178, filed Mar. 11, 2009 and from provisional patent application 61/257,483, filed Nov. 3, 2009, and is a continuation in part of patent application Ser. No. 12/082,507, filed Apr. 11, 2008 now abandoned which claims priority from provisional application Ser. No. 60/913,489, filed Apr. 23, 2007 and provisional application Ser. No. 61/008,100, filed Dec. 17, 2007. The entire contents of each of these applications are incorporated herein by reference.

BACKGROUND OF THE INVENTION

1. Technical Field

This application relates to a medical guidewire and more particularly to a medical guidewire system with adjustable size and stiffness.

2. Background of Related Art

Guidewires are currently being used in medical procedures to guide catheters, sheaths or other devices from a remote site to a surgical site. From a remote part of the body, a guidewire is introduced into an artery or vein. The guidewire is then advanced through the vascular system to the target site where an angiogram, balloon, stent, catheter or other vascular device is to be positioned. The guidewire then functions as a rail for advancement of these devices.

Currently, a soft small diameter wire, such as a 0.014 wire, is utilized initially to advance in the artery or vein. During advancement, especially through tortuous anatomy, the soft wire may lack the requisite pushability to advance around a curve. Also, due to its softness/flexibility, it may be difficult to advance a catheter over it to perform the surgical, e.g. diagnostic and/or interventional, procedure. In these instances, this flexible wire needs to be exchanged for a stiffer and/or larger wire. To exchange the guidewire, several steps are required. First, an exchange catheter is advanced over the soft wire. Second, the soft wire is removed. Third, the stiffer wire is inserted through the exchange catheter. Fourth, the exchange catheter is removed, leaving the stiffer wire in place. Such wire exchanges are time consuming and require two separate wires and an exchange catheter. Furthermore, these steps also increase risks to the patient such as increased risk of infection and increased chance of damaging the vessel due to the added insertion and removal of the wires through the vascular system as well as possible loss of wire position and critical time loss.

Even after exchange for the larger wire, sometimes the requisite stiffness and pushability to advance through a curved vessel portion is still lacking and therefore the wire needs to be exchanged for yet an even stiffer wire. This requires an additional wire exchange utilizing the time consuming four step method described above.

After such exchange for a stiffer wire and advancement around the tortuous portion of the anatomy, a stenosis or restricted passage of the vessel might be encountered through which the larger wire cannot pass. Thus, yet another catheter exchange could be required, this time exchanging the larger diameter stiffer wire for the smaller diameter softer wire. As a result, multiple guidewire exchanges requiring multiple insertions of the exchange catheter, multiple removals of the already inserted wire, and multiple insertions of a new wire from the remote site may be necessary in a single surgical (diagnostic and/or interventional) procedure. As noted above, this adds undesired time to the surgical procedure, as well as increases the risk of trauma or damage to the vessel and loss of desired wire position.

In addition, the inventor has found that in some instances where a catheter exchange is required, the surgical procedure cannot even be performed. That is, in some instances, the exchange catheter, which has a larger diameter (typically about 0.040 inches inside diameter) than the stiffer replacement wire because it has a lumen to receive the wire, cannot cross the stenosis. In this case, the guidewire with increased pushability cannot be inserted and advanced to reach the target site, thus not enabling a stent, dilation balloon or other vascular treatment device to be advanced to the surgical site. Consequently, the intralumenal surgical procedure cannot be performed.

As can be appreciated from the above, in the current procedure, multiple guidewires may be required to achieve desired parameters such as softness to reduce trauma to the vessel during insertion, reduced diameter to enable access through restricted passages in the vessels and facilitate access to the surgical site, stiffness/rigidity to allow pushability and stiffness/rigidity to facilitate passage of a catheter thereover. For example, a gentler more flexible guidewire, such as a 0.014 inch diameter wire, has the small diameter and softness advantage, but lacks the pushability to advance through some tortuous anatomy. The larger diameter guidewire, such as the 0.035 or 0.038 inch diameter guidewire, is more rigid and has better pushability but may be too large for restricted passages. It may also still lack the necessary stiffness, thus requiring an exchange for an extra stiff wire. The extra stiff wire lacks the flexibility and softness. Thus, the user needs to exchange the wires to obtain the requisite pushability, flexibility and stiffness for accessing the diagnostic and/or interventional site.

Also, exchange sheaths, when used with a 0.014 guidewire, present a relatively large stepped transition from their distal end to the smaller diameter 0.014 guidewire, therefore creating a more traumatic "snow plow" effect during insertion.

Therefore, it would be advantageous to provide a guidewire system which provides the desired diameter, pushability, flexibility and stiffness without requiring guidewire exchanges and exchange catheters, thereby eliminating the foregoing disadvantages of such exchanges.

It would also be advantageous if fluid, such as contrast, could be injected through the guidewire system for visualization.

SUMMARY OF THE INVENTION

The present invention overcomes the problems and deficiencies of the prior art. The present invention provides in one aspect a medical guidewire system comprising a first inner member having a first outer diameter, a second intermediate member having a second outer diameter larger than the first outer diameter, and a third outer member having a third diameter larger than the second outer diameter. The second member has a longitudinally extending opening to receive the first member for relative sliding movement with respect to the first member and the third outer member has a longitudinally extending opening to receive the second member for relative sliding movement with respect to the first and second member. The second and third members have an interlocking frictional engagement and the first and second members have a clamping engagement.

In one embodiment, the third member has a third stiffness greater than the first stiffness of the first member, and the second member is movable with respect to the third member to provide the third member with a second stiffness greater than the third stiffness.

In one embodiment, the first member comprises a solid core material. The first and second members in one embodiment are composed at least in part of shape memory metal. In one embodiment, the second and/or third members comprise hypotubes which can have slots in a sidewall to increase flexibility.

In one embodiment, the first member includes a slotted member slidable thereon for selected engagement with the second member at a selected position.

The present invention in another aspect provides a medical guidewire system comprising an inner member having an outer diameter and an outer member having an inner diameter, the inner diameter being larger than the outer diameter. The outer member has a longitudinally extending lumen to receive the inner member. The inner and outer members are relatively slidable to adjust a stiffness of the guidewire system. The lumen of the outer member forms a gap for fluid flow therethrough. A connector has a first end portion connected to the outer member, a second end portion connected to the inner member and a fluid infusion channel communicating with the gap for injection of fluid through the gap to exit a distal portion of the outer member.

The inner member can be selectively lockable with the outer member. The gap in one embodiment is defined by an annular space between an outer wall of the inner member and an inner wall of the outer member.

In one embodiment, the connector includes a first clamping member at the first end portion and a second clamping member at the second end portion. A rotatable knob can be provided at each end portion to provide a clamping force on the inner member and on the outer member. The connector can include a side arm for delivering fluid to the lumen of the outer member.

In one embodiment, the outer member comprises a hypotube having a plurality of slots formed therein.

In another aspect, the present invention provides a medical guidewire system comprising an inner member having an outer diameter, an outer member having an inner diameter forming a first lumen, and an intermediate member having a second lumen. The inner diameter is larger than the outer diameter. The outer member has a longitudinally extending lumen to receive the intermediate member and the intermediate and outer members are relatively slidable to adjust a stiffness of the guidewire system. The lumen of the intermediate member forms a gap for fluid flow therethrough, and a connector has a first end portion connected to the intermediate member, a second end portion connected to the inner member and a fluid infusion channel communicating with the gap for injection of fluid through the gap to exit a distal portion of the guidewire system. The connector includes a first clamping member engageable with the intermediate member and a second clamping member engageable with the inner member.

In one embodiment, the inner wire has a locking member thereon movable by engagement with the intermediate member to a locking position to fix the position of the inner and intermediate members, and the intermediate member has a flared handle portion frictionally engageable with the outer member to fix the position of the outer and intermediate members.

DETAILED DESCRIPTION OF THE DRAWINGS

Preferred embodiment(s) of the present disclosure are described herein with reference to the drawings wherein:

FIG. 1 is a perspective view of the guidewire system of the present invention showing the intermediate (stiffener) wire and outer wire in the retracted position to expose the inner wire;

FIG. 1A is an exploded perspective view of the guidewire of FIG. 1;

FIG. 1B is a longitudinal cross-sectional view of the guidewire of FIG. 1 showing the outer wire and the intermediate stiffener wire in the advanced position;

FIG. 2 is a perspective view of an alternate embodiment of the guidewire system of the present invention showing the intermediate (stiffener) wire and outer wire in the retracted position to expose the inner wire;

FIG. 2A is a longitudinal cross-sectional view of the guidewire of FIG. 2 showing the outer wire and the intermediate stiffener wire in the advanced position;

FIG. 3 is an anatomical view illustrating the guidewire of the present invention being inserted through the femoral artery for subsequent advancement through the vascular system, e.g. to the external carotid artery (the shuttle sheath not shown for clarity);

FIG. 4 is a longitudinal cross-sectional view of the guidewire of FIG. 1 showing the outer wire and the intermediate stiffener wire in the retracted position to expose the inner wire, corresponding to the position of the wires in FIG. 1;

FIG. 5 is a longitudinal cross-sectional view of the guidewire of FIG. 1 showing the outer wire in the advanced position and the intermediate stiffener wire in the retracted position;

FIG. 6 is a perspective view of an alternate embodiment of the guidewire of the present invention having a modified distal tip, and illustrating the outer wire and intermediate stiffener wire in the retracted position to expose the inner wire;

FIG. 7 is a longitudinal cross-sectional view of the guidewire of FIG. 6 except showing the outer wire in the advanced position and the intermediate wire in the retracted position;

FIG. 8 is a perspective view of a proximal end of the guidewire of the present invention showing attachment of a conventional extension wire to the inner wire;

FIG. 9 is an enlarged cross-sectional view taken along line 9-9 of FIG. 8 showing the attachment of the extension wire to the inner wire;

FIG. 10 is a perspective view of another alternate embodiment of the guidewire system of the present invention, the outer wire shown in the advanced position and the intermediate stiffener wire in the retracted position;

FIG. 11 is a longitudinal cross-sectional view of the guidewire of FIG. 10 showing the outer wire in the advanced position and the intermediate stiffener wire in the retracted position;

FIG. 12 is a cross-sectional view of an alternate embodiment of the handle of the inner wire having a threaded engagement for removal from the inner wire;

FIG. 13 is a perspective view of an alternate embodiment of the guidewire system of the present invention showing the intermediate (stiffener) tube and outer tube in the retracted position to expose the inner wire;

FIG. 13A is a cross-sectional view taken along line A-A of FIG. 13 showing the distal region of the outer tube (the inner wire removed for clarity);

FIG. 13B is an exploded perspective view of the guidewire of FIG. 13;

FIG. 14 is an enlarged view of the guidewire of FIG. 13 showing the handles in the retracted unlocked position;

FIG. 15 is a perspective view of the inner wire handle of FIG. 14 engaged (interlocked) with the stiffener handle prior to locking;

FIG. 16 is a perspective view similar to FIG. 15 showing the inner wire handle rotated to lock the inner wire and stiffener;

FIG. 17 is an enlarged view of the stiffener tube of FIG. 13;

FIG. 18 is an enlarged view of an alternate embodiment of the stiffener tube;

FIG. 18A is an enlarged view of an alternate embodiment of the outer tube;

FIG. 18B is an enlarged view of an alternate embodiment of the outer tube;

FIG. 19 is an enlarged perspective view of a proximal portion of an alternate embodiment of the guidewire system of the present invention showing the inner wire and stiffener tube in the retracted position;

FIG. 20 is a perspective view showing the handles of FIG. 19 prior to engagement;

FIG. 21 is a cross-sectional view of the handle of the inner wire of FIG. 19 prior to attachment to the inner wire;

FIG. 22 is an enlarged perspective view of a proximal portion of another alternate embodiment of the guidewire system of the present invention showing the inner wire and stiffener in the retracted position;

FIG. 22A is an enlarged view of the locking member of the inner wire of FIG. 22;

FIG. 23 is a cross-sectional view illustrating the threaded locking member of the inner wire spaced from the threaded portion of the stiffener collar;

FIG. 24 is a cross-sectional view of the threaded locking members engaged for rotation to fix the inner wire axially with respect to the stiffener tube; and FIG. 25 is a perspective view of a proximal portion of another alternate embodiment of the guidewire system of the present invention showing the inner wire in the retracted position;

FIG. 26 is a perspective view of another alternate embodiment of the guidewire system of the present invention;

FIG. 27 is a close up perspective view of the threaded interlock of the intermediate and outer members of FIG. 26;

FIG. 28 is a close up perspective view of the clamping interlock of the intermediate and inner members of FIG. 26;

FIG. 29 is a cross-sectional view of an alternate embodiment of the guidewire system of the present invention having a connector for fluid injection;

FIG. 29A is a perspective view of the inner wire, intermediate and outer tube of FIG. 29;

FIG. 30 is a cross-sectional view of another alternate embodiment of the guidewire system of the present invention having a connector for fluid injection;

FIG. 31 is a cross sectional view of the distal portion of the guidewire system of FIG. 30 showing the inner member in an advanced position.

DETAILED DESCRIPTION OF PREFERRED EMBODIMENTS

Turning now to the drawings, wherein like reference numerals identify similar or like components throughout the several views, the guidewire system of the present invention is illustrated. The guidewire system comprises a guidewire 10 have three coaxial members, or in some embodiments two coaxial members, movable with respect to one another to adjust the stiffness and size (outer diameter) of the guidewire.

More specifically, the guidewire system 10 in the embodiment shown in FIGS. 1-5, comprises a small diameter inner member 20, an intermediate stiffener member 30 slidable over the inner member 20, and a larger diameter outer member 40 slidable over the intermediate member 30 and the inner member 20. As used herein, the term "proximal" refers to the part or component of the system closer to the user and the term "distal" refers to the part or component further from the user. The term member as used herein includes a wire, tube or other structure of the inner, intermediate and outer components of the guidewire system.

The small diameter inner member 20, in a first embodiment, is a wire having a spherical or ball tip 22 either integral or attached thereto. The ball tip 22 provides a blunt atraumatic leading end of the wire to reduce trauma to the vessel during advancement. The ball tip 22 is also preferably dimensioned so it has a larger diameter (transverse dimension) than the diameter of the lumen 42 of the outer wire 40 or at least larger than the diameter of the opening to the lumen 42. Thus, it also acts as a stop to prevent withdrawal of the entire wire 20 through the outer wire 40 and acts as a stop to limit distal movement of the outer wire 40 so it does not extend over the tip 24 so that a blunt tip can remain as the leading edge for the guidewire 10 to provide a smoother passage. This is shown for example in FIG. 2 where the surface 22a of the tip 22 would abut the distalmost end 40a of outer wire 40.

It should be appreciated that tips other than ball tips can be utilized. For example, FIGS. 6 and 7 show a conical tip 22' of inner wire 20' having a smother transition and functioning similar to ball tip 22. In all other respects, guidewire 10' of FIG. 6 is identical to the guidewire 10 of FIG. 1. The guidewire 10' is shown in FIG. 6 with the intermediate wire 30' and outer wire 40' retracted to expose the inner wire 22' and shown in FIG. 7 with the outer wire 40' advanced to its distal position.

Additionally, it should be appreciated that an enlarged tip need not be provided. For example, in the alternate embodiment of FIG. 2, the distal tip of the inner wire is the same diameter as the portion proximal of the distal tip.

The inner wire forms the core wire of the system, and is preferably formed of a solid core and can be composed at least in part of a shape memory material such as Nitinol. Non-metallic materials can also be utilized, such as Pebax. The inner wire in one embodiment can have a coil and core combination towards its distal end and is a solid wire towards it proximal end. Other materials such as stainless steel are also contemplated. Preferably the wire 20 has an outer diameter of about 0.014 inches, although other dimensions are also contemplated. Preferably, the inner wire 20 has a greater degree of flexibility and is softer than the other two wires 30, 40. In one embodiment, for example, the coil wire is composed of a stainless steel wire with a platinum coil at a distal tip over a reduced diameter of the stainless steel wire, and has a PTFE coating.

The stiffener member 30 forms the intermediate wire as it is positioned between the inner wire 20 and outer wire 40. Stiffener wire 30 can be formed from single or multiple wires wound together, having a lumen 32 with a dimension (diameter) larger than the outer diameter of the wire 20 so it can slide over wire 20 (or wire 20 can slide within it). In a preferred embodiment, the stiffener wire 30 has an outer diameter of about 0.018 inches, although other dimensions are also contemplated. The wire 20 can be formed of a shape memory material such as Nitinol, although other materials, such as stainless steel, are also contemplated. In one embodiment, the stiffener has a stiffness/rigidity greater than the stiffness of the inner wire 20 and outer wire 40. However, the stiffener can alternatively have a stiffness less than the stiffness of the outer wire/and or inner wire, provided it has sufficient stiffness such that when it is advanced, it stiffens a distal region of the outer wire (and overall guidewire system) by providing a distal region of increased wall thickness due to the combination of stiffener and outer member. That is, in such embodiment, advancement of the stiffener provides a thicker walled and thereby stiffer/more rigid wire.

The stiffener, in an alternate embodiment, is in the form of a slotted hypotube which is described in more detail below.

The outer wire 40 has a longitudinally extending opening or lumen 42 with a dimension (diameter) larger than the outer diameter of the intermediate wire 30 so it can slide over wire 30 and smaller wire 20 (or wire 30 can slide within it). In a preferred embodiment, the outer diameter of the wire is between about 0.035 inches to about 0.038 inches, although other dimensions are also contemplated. In one embodiment (not shown) the outer wire 40 is a wound wire wound in one direction. It could be a round wire or a rectangular wire. Alternatively, it can comprise a series of wound or twisted wires. The wire 40 can also have a hydrophilic and/or a PTFE coating. It can also be formed with a coated or uncoated plastic jacket. A safety wire connected to proximal and distal portions of the outer wire could optionally be provided. The outer wire 40 has a stiffness/rigidity greater than the stiffness of the inner wire 20. In some embodiments, the outer wire can also have a stiffness less than the stiffness/rigidity of the intermediate wire 30 as discussed above.

In an alternate embodiment, the outer tube is in the form of a slotted hypotube which is described in more detail below.

In the alternate embodiment of FIGS. 2 and 2A, inner wire 50 does not have an enlarged tip but terminates in a tip 52 of the same diameter. Outer wire 60 has a thicker wall portion at the distal end portion 62 to create a shoulder 62*b* and a reduced lumen diameter 62*a*. The shoulder 62*b* can form a stop to limit distal advancement of the stiffener 70 such that the distalmost end of the stiffener, although extending to a distal region of the outer wire 60, cannot extend to a distalmost end of the outer wire 60. The reduced lumen area 62*a* creates a tighter fit for the inner wire 20 as it slides more closely around the inner wire 50 to limit entry of material into the lumen of the outer wire 60. The tighter fit also enables clot to be wiped off the inner wire 50 upon movement with respect to the distal tip 63 of outer wire 60. The tip 63 also has a smooth shallow taper (similar to the outer wire 40 of FIG. 1) to provide a smoother transition and facilitate advancement over the inner wire 50 in very tight and tortuous anatomy with reduced trauma. Tips with even more gradual tapers could be provided. In all other respects, the guidewire system of FIG. 2 is the same as FIG. 1.

In one embodiment, the inner wires described herein have a length of about 3.0 m, the intermediate wires or tubes described herein have a length of about 2.36 m to about 2.38 m and the outer wires or tubes described herein have a length of about 2.4 m to about 2.6 m. In another embodiment, the intermediate wires or tubes described herein have a length of about 1 m to about 2 m, and preferably about 1.8 m, and the outer wires or tubes described herein have a length of about 1 m to about 2 m, and preferably about 1.8 m. It should be understood that these dimensions are provided by way of example and other dimensions are also contemplated.

It should be appreciated that sliding movement of the wires (or tubes) referred to herein means that either the outside wire (or tube) is moving over the held (stationary) inside wire, the inside wire is moving within the stationary outside wire, or both wires are sliding in opposite directions. For example, the inner wire can be exposed by moving the inner wire distally, moving the outer wire (tube) proximally, or moving both wires in their respective directions. However, it may be preferable that the stiffening wire be advanced or retracted to maintain the advanced position of the guidewire during insertion. The foregoing likewise applies to the use of tubes instead of wires as one or more of the members of the guidewire system.

The use of the guidewire system will now be described with reference to the embodiment of FIG. 1, it being understood that such use is also applicable to the other embodiments of the present invention described herein utilizing the three members in the form of wires or tubes (or other structures).

It is also contemplated that a two component guidewire system be provided with an inner member and an outer member slidable with respect to one another to adjust the guidewire diameter and to adjust the guidewire stiffness without the use of a stiffener. The inner member and outer member in such system are lockable to one another. Examples of such embodiments are described below.

In use, selective positioning of the three wires with respect to one another varies the diameter of the guidewire being advanced through the vascular system and varies the stiffness of the guidewire. This independent sliding movement of the wires provides an in situ progressive transformation of the soft wire, used to avoid damage to the vessel, into a stiff or rigid wire to provide a rail system for easier catheter advancement thereover and to increase pushability around curved anatomy.

More specifically, to increase the pushability and stiffness of the guidewire 10, the outer wire 40 is advanced distally over the inner wire 20 from the position of FIG. 4 to the position of FIG. 5 (or the inner wire 20 is retracted to the position of FIG. 5). If further stiffness or enhanced pushability is desired, the intermediate wire 30 is advanced from the retracted position of FIG. 5 to the advanced position of FIG. 1B. Sliding of the wires is controlled by the user at the proximal end.

Note in the embodiment of FIG. 1B, in the advanced position of the intermediate wire 30, it remains spaced proximally from the distalmost end of the outer wire 40 to reduce trauma to the vessel by ensuring some flexibility of the distalmost tip of the guidewire 10. In one embodiment, in the advanced position, the distalmost end 34 of the intermediate wire 30 is spaced a distance of about 1 centimeter to about 4 centimeters, and preferably from about 1 cm to about 2 cm, from the distalmost end 40*a* of outer wire 40. Other spaced distances are also contemplated. In the advanced position of the inner wire 20 (FIGS. 1 and 4), it can protrude about 30 cm to about 40 cm from the distalmost end 40*a* of outer wire 40. In other embodiments, it can protrude from about 5 cm to about 20 cm from the distalmost end 40*a* of outer wire 40. Other protruding lengths are also contemplated.

After the guidewire 10 has been stiffened by relative sliding movement of the outer and/or intermediate wire, if a smaller diameter and more flexible guidewire is desired, the inner wire 20 can again be exposed by retraction of the outer wire 40 (and stiffener wire 30) or advancement of the inner wire 20 (or opposite movement of both).

As can be appreciated, relative movement of the wires can occur repeatedly as desired to enhance advancement of the guidewire 10 though the vascular system to the desired surgical site.

In an alternate embodiment shown in FIGS. 10 and 11, each of the wires 120, 130 and 140 of guidewire 100 has a handle portion. Handle portions as used herein include integral handles, separate handles attached to the members or a proximal end portion of the member which interlocks with another member. With reference to FIGS. 10 and 11, inner wire 120 has a handle 124 at its proximal end, intermediate stiffener wire 130 has a handle 134 at its proximal end, and outer wire 140 has a handle portion 144 at its proximal end. This facilitates grasping of the wire by the user as well as facilitates torquing of the wire to rotate the distal end. One or more of the handles can include a textured surface (see e.g. handle 144 of FIG. 10) to facilitate gripping.

The handles can optionally interlock to fix the positioning of the wires with respect to one another. FIG. 11 illustrates one way to interlock the handles. In this embodiment, the engagement regions of the members include an interlocking feature in the form of a taper/recess interlock. More specifically, interlocking is achieved by providing a taper on the distal portion of handles 124 and 134 which frictionally mate with a proximal recess at the proximal end of the mating handle. More specifically, distal tapered region 125 of handle 124 would frictionally engage with the proximal recess 136 of handle 134 and distal tapered region 135 of handle 134 would frictionally engage the proximal recess 146 of handle 144. Thus, when inner wire 120 is moved relative to the outer wire 140, the user does not need to hold it in this advanced (exposed) position as the handle 124 would interlock with handle 134 to fix the inner wire 120 in position. Similarly, when intermediate wire 130 is moved relative to the outer wire 140, the user does not need to hold it in this position as the handle 134 would interlock with handle 144 to fix the inner wire 120 and intermediate wire 130 in position. This interlocking of the handles 134 and 144 could also be used to maintain the spacing between the distalmost ends of the wires 130 and 140 as described above with respect to wires 30 and 40. It could also be used to maintain the distal tip of the inner wire 20 as the leading edge instead of or in addition to utilizing the larger diameter tip, e.g. the ball tip, to achieve this function. The handle for the outer wire is shown as the same dimension of the outer wire so the handle can be considered the proximal portion of the wire.

FIGS. 13-17 illustrate an alternate embodiment of the guidewire system having alternate engagement regions providing an alternate mechanism for interlocking the members. This system has a stiffener and outer member formed of a tube. The relative stiffness of the inner, intermediate, and outer members can be provided as discussed above.

More specifically, guidewire 210 has an inner member 220, an intermediate stiffening member 230 and an outer member 240. Stiffener member 230 is in the form of a tube, preferably composed of stainless steel, and has a longitudinally extending lumen 232 (FIG. 17) dimensioned to slidingly receive inner wire 220. The stiffener tube 230 in the embodiment illustrated in FIG. 17 has a plurality of slots 234 formed therein (preferably laser cut into the tube) to increase the flexibility of the tube. Each slot in the illustrated embodiment, extends around a portion of the circumference, for less than 360 degrees and preferably less than 180 degrees. Additionally, the slots are staggered such that a solid portion of the tube between the space between slots in one row is adjacent a slotted portion of another row. For ease of understanding, three rows of slots have been numbered in FIG. 17 to illustrate how slot portion 236a of row R2 is adjacent a gap 235b (solid tube portion) between slot portions of row R1 and adjacent gap 237b (solid tube portion) between slot portions of row R3.

As shown, the axial spacing between the slots in FIG. 17 is substantially equal. However, it is also contemplated that the spacing between the slots can be varied at various portions along the tube to provide areas of different flexibility. For example, in the embodiment of FIG. 18, the slots of tube 230' vary such that slots 231a at the distal portion of the tube 230' are closer together (have a shorter distance d1) than the slots 231b of a more proximal portion which have a greater distance d2 between them. This provides more flexibility toward the distal end. Various slot spacing is contemplated. For example, the slots can be varied such that they become progressively further apart in a proximal direction or discrete regions of the tube can have slots of substantially equal spacing, but different than other regions of the tube.

It is also contemplated, that the slots can be formed in a spiral pattern such as shown in FIG. 18A illustrating an outer tube with slots. The outer tube 240' has spiral or helically arranged slots 249 formed in the tube, preferably at an angle to the longitudinal axis as shown. The spiral slots, preferably formed by laser cutting, can be interrupted, leaving a solid wall portion 243 between the sets of spiraling slots. The solid wall portions can be evenly spaced as shown to provide similar sets of slots or can be varied to provide sets having different lengths of spiraling slots. Such spiraling slots can also be formed on the intermediate stiffener tube. A heat shrink tube (not shown), made of PET for example, can be positioned over all or a portion of the tube, and preferably over a distal portion and a hydrophilic coating or jacket can be provided over the distal portion, preferably for about 30 cm.

In the embodiment of FIG. 18B, gaps 262b (solid tube portion) of slots 260 are radially staggered. The slots 260 are formed in a spiral pattern with the space 263 therebetween (pitch) increased toward a proximal end. Different portions can be of a different constant pitch and/or portions can be of progressively increasing pitch.

The foregoing slot arrangements can be provided on the stiffener tube and/or the outer tube. It should be appreciated, however, that in alternate embodiments, the stiffener tube and/or outer tube do not have slots.

Referring back to FIGS. 13-13C, inner wire preferably is a 0.014" wire as described above and outer member 240 is in the form of a tube, preferably of stainless steel. The outer tube 240 can have slots in the various arrangements as described above with respect to the stiffener tube 230 and the distances between slots can be varied in different regions of the tube as described above. The outer tube 240 and stiffener 230 can have the same or different slot arrangements.

Outer tube 240 has a lumen 242 dimensioned to slidingly receive stiffener tube 230. Outer tube 240 has a distal end portion, best shown in FIG. 13A, having a distal lumen portion 242a that gradually reduces in diameter, to a diameter E1 at region 242b, less than the diameter E2 at region 242c. In this manner, diameter E1 can be close to the outer diameter of the inner wire 230 to reduce any gap between the inner wire 220 and outer tube 240 when the inner wire 220 is extended. The inner wall 241 of outer tube 240 is angled to provide a smooth transition between the two diameters E1 and E2 to ease the movement of inner wire 220 through lumen 242 to an extended position.

Alternatively, a lead in tube, e.g. tube 850 of FIG. 31, can be positioned within the outer tube at a distal end having a reduced diameter portion for the inner member. The lead in tube can be attached to the outer tube by soldering, e.g. solder 860, or other attachment methods. Solder 860 can have a radiused portion to provide a smooth transition for sliding of the inner wire 820 through outer tube 840. The lead in tube is shown with the embodiment having a fluid connector (described below), but could also be used in other embodiments described herein.

In some embodiments, a distal portion of the outer tube can have a PET heat shrink and/or a hydrophilic coating. The PET can have a hydrophilic coating over a distal portion. Proximal of the distal portion a coating such as PTFE can be provided on the outer tube.

The members in the embodiment of FIGS. 13-16 have engagement regions with an interlocking feature in the form of a rotational pin and slot arrangement. More specifically, inner wire 220 has a handle 221 with an L-shaped slot 228 at its distal end. Pin 233 at the proximal end of handle 231 of stiffener tube 220 engages slot 228. That is, when the inner wire 220 is advanced longitudinally, the pin 233 engages the longitudinal region 228a of slot 228 (see FIG. 15). This also acts as a stop for longitudinal advancement of the inner wire 220. Once in the slot region 228a, the inner wire 220 is rotated so that the pin 233 enters the transverse slot region 228b as shown in FIG. 16, thereby fixing the axial position of the inner wire 220 and stiffener 230. Similarly, the intermediate tube 230 has an L-shaped slot 238 at the distal end of handle 231. A proximal pin 245 of outer tube 240 enters the longitudinal slot region 238a and then upon rotation, enters the transverse region 238b to fix the stiffener 230 to the outer tube 240. Pin 245 could also be provided on a handle of outer tube 240. This interlocking handle also functions as a stop to limit the extent of distal movement of the stiffener tube 230 within outer tube 240.

Note as an alternative to the pin/slot arrangement, two locking tabs could be provided as shown in FIG. 25. Mating tabs 292 and 283 of outer tube 290 and of handle 281 of stiffener tube 280, respectively, interlock upon rotation. Similarly, proximal locking tab 282 of handle 281 of stiffener tube 280 interlocks with tab 272 of handle 271 of inner wire 270.

FIGS. 19-21 illustrate another embodiment for interlocking the handles to lock the members to prevent longitudinal movement of the members. The embodiment is similar to the embodiment of FIG. 11. Inner wire 320 has a proximal handle 321 with a distal tapered region 322. This tapered region 322 is inserted into the opening 333 of proximal handle 331 of stiffener tube 330 to frictionally engage the handles. This interference fit interlocks the handles which thereby interlocks the inner wire 320 and stiffener tube 330 to prevent movement of the inner wire 320 with respect to the stiffener tube 330. The proximal end of outer tube 340 has an opening 343 dimensioned to matingly receive the distal tapered region 332 of handle 331 of intermediate stiffener tube 330 to lock the stiffener 330 against longitudinal movement with respect to the outer tube 340.

The handle 321 of inner wire 320 can include a distal taper 327 to releasably engage the inner wire 320, as shown in FIG. 21. In this manner, the handle 321 can be removed from the wire 320 to enable removal of the intermediate tube 330 and outer tube 340 from the surgical site by sliding proximally over the wire 320, leaving wire 320 in place. The proximal end of the handle 321 can include a lumen 328 to engage an extension wire (not shown) to increase the length of the inner wire 320.

Alternately, a torque type handle can be used to control the inner wire and can be positioned at a desired portion along the proximal exposed wire and can be configured so as to lock and unlock on the other wires while at the same time engaging the handle of the other wire. FIGS. 22-24 illustrate an example of this showing another alternate embodiment of an engagement region with an interlocking feature. A collet 422 has a distal tapered region with a plurality of slots 423. A series of external threads 424 threadingly engage internal threads 434 of collar 432. Collar 432 is attached to a proximal end of the stiffener tube 430.

In use, collet 422, which encircles inner wire 420, is inserted within the opening 435 of handle or collar 434. In this position, collet 422 is attached to collar 434 but inner wire 420 can still freely move longitudinally within intermediate stiffener tube 430 and outer tube 440. If the user decides to fix (lock) the position of the inner wire 420 to prevent longitudinal movement, handle surface 426, preferably textured to enhance grasping, is gripped and rotated as shown in FIG. 24. This advances the collet 422 further into the collar 432, resulting in the internal taper of the collar compressing the slotted region of the collet 422 to apply a clamping force on the inner wire 420. This clamping force applied by the collet 424 prevents longitudinal movement of the inner wire 420. To free the inner wire 420 for longitudinal movement, the collet 424 is rotated in the opposite direction to retract the collet 424 to allow it to expand to loosen the grip on the inner wire 420. Thus, the inner wire 420 and stiffener tube 430 can be selectively interlocked at a desired axial position of these members. That is, after movement of the members to the desired axial position, the user can rotate the collet the lock the members.

In the alternate embodiment of FIGS. 26-28, the proximal end 531 of handle 538 of intermediate stiffener tube 530 is dimensioned to receive collapsible slotted member or collet 522 which encircles inner wire 520. More specifically, slotted member 522 has a tapered region 525, progressively decreasing in diameter toward a distal end, and an elongated slot or slots 524 formed therein and extending through the slotted member 522. That is, slot 524 can be formed so it extends through the opposing wall to form an opposing slot, also labeled as slot 524 in FIG. 28 and shown in phantom. The slots 524 are illustratively shown extending substantially longitudinally and equidistantly spaced, but could alternatively extend in other orientations and spacings, and a different number of slots can be provided to achieve the collapsibility and clamping function. Slotted member 522 has a longitudinal opening 523 extending along its length to receive the inner wire 520 therethrough.

In the normal non-collapsed position, the longitudinal opening 523 of slotted member 522 has a dimension larger than the outer diameter of the inner wire 520 so the inner wire 520 can freely slide therethrough. When it is desired to lock the position of the inner wire 520 with respect to the intermediate or stiffener tube 530, the slotted member 522 is slid over the inner wire 520 and inserted into the opening 527 at the proximal end 531 of handle 538 of intermediate tube 540. Due to the internal diameter of the handle 538, when the slotted member 522 is inserted a sufficient distance, the wall of the handle 538 will apply a clamping force on the slotted member 522, thereby collapsing it around the inner wire 520 to reduce the diameter of the longitudinal opening 523 and provide a clamping force to prevent longitudinal movement of the inner wire 520. Thus, the user can selectively lock the members when desired to fix their axial position. When it is desired to free the inner wire 520 for longitudinal movement, the slotted member 522 is moved in the opposite direction, freeing itself from the confines of the handle 538 to allow it to expand back to its normal position (return the longitudinal opening to its larger diameter) to loosen the grip on the inner wire 520. In a preferred embodiment, the slotted member 522 is made from a superelastic material such as Nitinol to ensure repeated return to the previous configuration after repeated locking (clamping) and unlocking. Other materials are also contemplated. This Nitinol lock 522 can be slid proximally over the inner wire 520 and removed to enable removal of the outer tube 540 and intermediate tube 530 by sliding these tubes proximally over the inner wire 520.

In a two component system (without a stiffener), the slotted member 522 on the inner member would slide into a proximal portion of the outer tube (similarly dimensioned to handle 538) for clamping and locking of the outer tube and inner member.

A threaded engagement as shown in FIG. 26 fixes the position of the intermediate stiffener tube 530 and the outer tube 540. More specifically, the proximal end 542 of outer tube 540 has a series of male threads 546. These threads engage the internal female threads 537 on the distal end 536 of the handle 538 attached to or integral with the stiffener tube 530 to interlock the outer tube 540 and stiffener tube 530.

In all other respects, the guidewire system of FIGS. 26-28 and components and methods of use are the same as that described herein with respect to the other embodiments. The engagement regions (mechanisms for interlocking the members) of FIGS. 26-28 can be used with the various embodiments of the members described herein, including for example the slotted stiffener and outer hypotubes.

In an alternate embodiment illustrated in FIG. 29A, the proximal end 741 of outer tube 740 is crimped to form a reduced diameter portion and a distal end of intermediate tube 630 is flared out at region 738 to form a handle to be fitted over proximal end 741 to provide frictional (locking) engagement between the intermediate tube 630 and outer tube 740. In one embodiment by way of example, the outer tube can have a diameter of about 0.035 inches and is crimped down to about 0.033 inches and the intermediate tube has an attached tube portion with a flared portion of about 0.035 inches in diameter welded to the proximal end of the intermediate tube. This is described in more detail below, for example with the guidewire system having a fluid connector, but can be used with other systems.

FIG. 29-31 illustrate alternate embodiments of the guidewire system which enables fluid flow through the distal tip. Referring initially to FIG. 29, the three component guidewire system 600 is similar to the aforedescribed embodiments as it includes an inner member 620, an intermediate member (stiffener) 630 and an outer member 740. The intermediate member 630 and/or the outer member 640 are preferably in the form of a hypotube with slots in the form as shown in FIG. 18 or 18B, but other slot arrangements are also contemplated. The three members move with respect to each other in the manner described above to change the stiffness and diameter of the guidewire and therefore for brevity are not repeated herein. Further, the members can interlock in the various ways described above, also for brevity not repeated herein.

The guidewire system 600 of FIG. 29 differs from the aforedescribed guidewire systems in the provision of fluid injection. More specifically, guidewire system 600 includes a connector 700, preferably a Touhy Borst type connector, having a proximal end portion 702 and a distal end portion 704. The proximal end portion 702 includes external threads 706 which mate with internal threads 708 of proximal knob 710. Rotation of proximal knob 710 in a first direction compresses the proximal end portion of the connector 700 which in turn compresses internal collar 712 to apply a clamping force thereon. Internal collar 712 also provides a seal and has an opening to receive inner member 620 therethrough. Thus, rotation of proximal knob 710 in a first direction clamps the proximal end portion 702 of connector 700 to an intermediate portion of the inner member 620.

The distal end portion 704 of connector 700 includes external threads 726 which mate with internal threads 728 of distal knob 721. Rotation of distal knob 721 in a first direction compresses the distal end portion of the connector 700 which in turn compresses internal collar 722 to apply a clamping force thereon. Internal collar or seal 722 has an opening to receive a proximal end of intermediate member 630 therethrough. Thus, rotation of distal knob 721 in a first direction clamps the distal end portion 704 of connector 700 to the proximal end of the intermediate member 630. In this manner, the connector 700 is attached to a proximal end of the intermediate member 630.

The connector 700 includes a side arm 730 in fluid communication with the internal channel 703 of the connector 700. This internal channel 703 is in fluid communication with the proximal opening 632 in intermediate member 630. Consequently, fluid injected through the side arm 730 flows into internal channel 703, through the proximal opening 632 in intermediate member 630 and through the gap 634 defined as the annular space between the inner wall of the intermediate stiffener 630 and the outer wall of the inner member 620. The fluid flows through this gap or lumen, and out the distal end of the outer member 640.

In an alternate embodiment of the guidewire system illustrated in FIGS. 30 and 31, a two component guidewire system is provided. The two component guidewire system 800 includes an inner member 820 and an outer member 840, preferably in the form of a slotted hypotube similar to hypotube 740. In this simplified construction, relative movement of the inner member 820 and outer member 840 adjusts the diameter of the guidewire and adjusts the stiffness of the guidewire without the use of an intermediate stiffener tube. That is, if a smaller and more flexible guidewire is desired, the inner member, e.g. a 0.014 wire, can be advanced/exposed relative to the outer member 840. If a stiffer guidewire is desired, the outer member 840 is advanced over the inner member 820, while preferably maintaining the position of the inner member 820. This two component system can be utilized with the fluid injection connector and capabilities of FIGS. 30 and 31 as well as with guidewire systems without such connectors. In the two component system, the inner member would lock to the outer member rather than the stiffener (intermediate tube). This can be achieved in the manners described above with respect to the engagement of the inner member and stiffener. For example, a collet or slotted member similar to slotted member 522 of FIG. 28 on the inner member can be clamped by the handle portion of the outer member as it is selectively inserted therein. The slotted member would be approximately sized for such engagement.

In the embodiment of FIGS. 30 and 31, the two component system 800 has a connector 900 similar to connector 700 of FIG. 29. More specifically, connector 900, preferably a Touhy Borst type connector, has a proximal end portion 902 and a distal end portion 904. The proximal end portion 902 includes external threads 906 which mate with internal threads 908 of proximal knob 910. Rotation of proximal knob 910 in a first direction compresses the proximal end of the connector 900 which in turn compresses internal collar 912 to apply a clamping force thereon. Internal collar 912 also provides a seal and has an opening to receive inner member 820 therethrough. Thus, rotation of proximal knob 910 in a first direction clamps the proximal end portion 902 of connector 900 to the inner member 820.

The distal end portion 904 of connector 900 includes external threads 926 which mate with internal threads 928 of distal knob 921. Rotation of distal knob 921 in a first direction compresses the distal end portion 904 of the connector 900 which in turn compresses internal collar 922 to apply a clamping force thereon. Internal collar or seal 922 has an opening to receive outer member 840 therethrough. Thus, rotation of distal knob 921 in a first direction clamps the distal end portion 904 of connector 900 to the outer member 840. In this manner, the connector 900 is attached to a proximal end of the outer member 840.

The connector 900 includes a side arm 930 in fluid communication with the internal channel 903 of the connector 900. This internal channel 903 is in fluid communication with the proximal opening 842 in outer member 840. Consequently, fluid injected through the side arm 930 flows into internal channel 903, through the proximal opening 842 in outer member 840 and through the gap 844 defined as the annular space between the outer wall of the inner member 820 and the internal wall of the outer member 840. The fluid flows through this gap or lumen space, exiting the distal end of the outer member 840. This provides an increased gap diameter compared to the three component system of FIG. 29 because of the absence of the smaller diameter stiffener tube.

Various types of fluids can be injected through the guidewire systems. One type of fluid that can be injected is a radiopaque contrast for angiographic visualization. Other types of fluids include but are not limited to embolics and drugs. It is also contemplated that the inner wire can be removed to provide a larger lumen for injection of fluids or materials such as bioglues, microspheres, microbeads and/or embolic coils. Note that with the inner wire removed, proximal knob 910 (or knob 710) can be rotated to clamp further on collar 912 to provide a seal.

It should also be appreciated that in preferred embodiments, the components (inner, intermediate and outer members) of the guidewire system of FIG. 26, as in the other preferred embodiments of the guidewire systems disclosed herein, do not exceed a diameter of about 0.038 inches, and more preferably do not exceed a diameter of about 0.035 inches.

In an alternate embodiment shown in FIG. 12, the inner wire handle 124' is removable from inner wire 120' by unscrewing. More specifically, handle 124' is attached to inner wire 120' by a screw thread 121' such that the handle 124' can be unscrewed from inner wire 120. This allows outer wire 140 and intermediate wire 130 to be removed by retraction (proximal movement) over the length of the inner wire 120', thereby leaving only the softer, smaller diameter wire in place.

A conventional extension wire W can optionally be attached to the inner wire 20 (or other inner wires described herein) by a friction fit as shown in FIGS. 8 and 9. That is, a recessed, portion of female taper of inner wire 20 receives a male tapered distal end W1 of extension wire W.

It is also contemplated that the outer and intermediate wires could be held in place and the inner wk removed and replaced with another 0.014 inches wire, such as a conventional 0.014 wire currently being used for surgical procedures.

The aforedescribed guidewires of the present invention provide a method of adjusting the stiffness and size of a guidewire without full withdrawal of the guidewire from a patient's vascular system. The use will be described in conjunction with guidewire 10, however it should be appreciated that the description is applicable to the other three components guidewire systems discussed herein.

In one method of use, the guidewire 10 is advanced into the vascular system from a remote site, such as the femoral artery F (see FIG. 3), with the outer wire 40 and stiffener 30 in the retracted position to expose a substantial length of the inner wire 10 to expose a smaller wire diameter as shown in FIGS. 1 and 4. This provides for increased flexibility of the guidewire system and less trauma to the vessel. Note it is also contemplated that the guidewire is inserted from other sites such as the jugular vein or radial artery.

After initial advancement of the guidewire 10 through the vascular system en route to the target site such as the carotid artery C (FIG. 3), if a tortuous vessel portion or other anatomy is encountered wherein the inner wire 20 lacks the requisite pushability and stiffness, the outer wire 40 is slid in a distal direction over the inner wire 20, while maintaining the position of the inner wire 20, avoiding the need to remove the inner wire 20 from the patient. This creates a stiffer guidewire to increase the pushability of the guidewire system 10 to enable it to advance through the curved vessel portion (see FIG. 5).

If during advancement, the outer wire 40 lacks the requisite pushability or stiffness to advance through a tortuous vessel portion or other anatomy, the stiffener 30 can be advanced in a distal direction within the outer wire 40 and over the inner wire 20 to increase the overall stiffness of the guidewire 10, as shown in FIG. 1B.

After advancing through the tortuous vessel, the stiffener 30 can be withdrawn if desired, leaving the more flexible outer wire 40 for advancement.

If during advancement of the guidewire 10 with outer wire 40 covering the inner wire 20 a restricted passage in the portion of the vessel is encountered such that the vessel lumen dimension is less than the outer diameter of the outer wire 40, the outer wire 40 can be retracted in a proximal direction to expose a substantial length of the inner wire 20. The smaller diameter inner wire 20 can then be used to advance through the restricted passage of the vessel lumen.

As can be appreciated, the wires can be slid relative to one another (as defined herein) during the advancement of guidewire 10 to the treatment site any number of times as desired to provide the requisite diameter size, flexibility and stiffness.

Once the treatment site is reached, the stiffener 30 and outer wire 40 can be slid proximally over the inner wire 20 and removed from the patient, e.g. by removing the interlocking component of the inner member, thereby leaving the inner wire 20 in the patient to function as a rail for over the wire catheter and/or device insertion. Alternatively, the guidewire 10 can remain in place with the larger diameter wire 40 functioning as a rail for over the wire catheter and/or device insertion. In certain embodiments, fluid can be injected through the guidewire.

Although the method of use was described in relation to guidewire 10, the other guidewires disclosed herein would be advanced in a similar fashion. In the embodiment with a handle, the handle or torquer would be removed if it was desired to remove the outer wire and stiffener.

Additionally, the method was described above with the guidewire system initially inserted so the inner wire extends from the outer wire. It is also contemplated that if a larger wire is desired for initial insertion, the guidewire system would be inserted with the inner wire retracted. Then the inner wire can be advanced to be exposed if a smaller size or increased pushability is desired.

The two component system works in a similar fashion except without a stiffener tube, relying on the interaction of the inner member and outer tube for diameter and stiffness/flexibility adjustment.

While the above description contains many specifics, those specifics should not be construed as limitations on the scope of the disclosure, but merely as exemplifications of preferred embodiments thereof. For example, one or more of the wires can contain a hydrophilic coating. Those skilled in the art will envision many other possible variations that are within the scope and spirit of the disclosure as defined by the claims appended hereto.

What is claimed is:

1. A medical guidewire having adjustable rigidity, comprising:
a first inner wire member having a first outer diameter and a closed distal tip,
a second intermediate wire member having a second outer diameter larger than the first outer diameter, and
a third outer wire member having a third diameter larger than the second outer diameter, the second wire member having a longitudinally extending opening to receive the first wire member for relative sliding movement with respect to the first wire member,
the first wire member movable between a retracted position and an advanced position,
the third outer wire member having a crimped proximal end forming a reduced diameter portion and a longitudinally extending opening to receive the second wire member for relative sliding movement with respect to the first and second wire members,
the second wire member having a flared portion at a distal end thereof to engage the reduced diameter portion of the third wire member for an interlocking frictional engagement, and the first and second wire members have a clamping engagement,
the interlocking frictional engagement and clamping engagement being configured to fix the relative longitudinal position of the first, the second, and the third wire members when the first wire member is in one of the retracted or advanced positions relative to the third wire member,
wherein the first inner wire member, second intermediate wire member and third outer wire member are each independently slidable relative to one another to change the overall diameter, stiffness, and degree of pushability in advancement of the guidewire system, without a need to exchange the system or a portion thereof, and together the members function as a unitary structure such that a proximal region of said guidewire permits a medical device to be longitudinally advanced to a desired location in a patient.

2. The guidewire of claim 1, wherein the first wire member has a first stiffness, the third wire member has a third stiffness greater than the first stiffness, and the second wire member being movable with respect to the third wire member to provide the third wire member with a second stiffness greater than the third stiffness.

3. The guidewire of claim 1, wherein the first wire member comprises a wire having a solid core for at least a majority of its length.

4. The guidewire of claim 1, wherein the first wire member includes a slotted member slidable thereon for selective engagement with the second wire member at a selected position of the first wire member with respect to the second wire member.

5. The guidewire of claim 4, wherein the slotted member has a reduced diameter region with at least one slot extending therethrough.

6. The guidewire of claim 1, wherein the third wire member comprises a hypotube having a series of slots formed in a sidewall to increase flexibility.

7. The guidewire of claim 1, wherein the second wire member comprises a hypotube having a series of slots formed in a sidewall to increase flexibility.

8. The guidewire of claim 6, wherein the space between the slots increases toward a proximal end of the hypotube.

9. The guidewire of claim 1, wherein a proximal end of the third wire member includes a reduced diameter portion engageable by the flared portion of the second wire member.

10. A medical guidewire having adjustable rigidity, comprising:
an inner wire member having an outer diameter and a closed distal tip, and
an outer wire member having an inner diameter larger than the outer diameter, the outer wire member having a longitudinally extending lumen to receive the inner wire member,
the inner wire member movable between a retracted position and an advanced position,
a locking engagement feature being configured to fix the relative longitudinal position of the inner and outer wire members when the inner wire member is in one of the retracted or advanced positions relative to the outer wire member,
the inner wire member and outer wire member being independently slidable relative to one another to change the overall diameter, stiffness, and degree of pushability in advancement of the guidewire, without a need to exchange the guidewire or a portion thereof, and together the members function as a unitary structure such that a proximal region of said guidewire permits a medical device to be longitudinally advanced to a desired location in a patient, the lumen of the outer wire member forming a gap for fluid flow therethrough, the guidewire further having a connector having a first end portion connected to the outer wire member, a second end portion connected to the inner wire member, and a fluid infusion channel communicating with the gap for injection of fluid through the gap to exit a distal portion of the outer wire member.

11. The guidewire of claim 10, wherein the inner wire member is selectively lockable with the outer wire member.

12. The guidewire of claim 10, wherein the gap is defined by an annular space between an outer wall of the inner wire member and an inner wall of the outer wire member.

13. The guidewire of claim 10, wherein the connector includes a first clamping member at the first end portion and a second clamping member at the second end portion.

14. The guidewire of claim 10, wherein the connector includes a rotatable knob at the first end portion to provide a clamping force on the inner wire member.

15. The guidewire of claim 10, wherein the connector includes a rotatable knob at the second end portion to provide a clamping force on the outer wire member.

16. The guidewire of claim 10, wherein the connector includes a side arm for delivering fluid to a lumen of the outer wire member.

17. The guidewire of claim 10, wherein the outer wire member comprises a hypotube having a plurality of slots formed therein.

18. A medical guidewire having adjustable rigidity, comprising:
an inner wire member having an outer diameter and a closed distal tip,
an outer wire member having an inner diameter forming a first lumen, and
an intermediate wire member having a second lumen, the inner diameter being larger than the outer diameter,
the inner wire member movable between a retracted position and an advanced position,
the outer wire member having a longitudinally extending lumen to receive the intermediate wire member, the lumen of the intermediate wire member forming a gap for fluid flow therethrough, the guidewire further having a connector having a first end portion connected to the intermediate wire member, a second end portion connected to the inner wire member and a fluid infusion channel communicating with the gap for injection of fluid through the gap to exit a distal portion of the guidewire, the connector including a first clamping member selectively engageable with a proximal portion of the intermediate wire member and a second clamping member engageable with the inner wire member, and wherein a looking engagement feature, the first clamping member and the second clamping member being configured to fix the relative longitudinal position of the inner, outer and intermediate wire members when the inner wire member is in one of the retracted or advanced positions relative to the outer wire member, the inner wire member, intermediate wire member and outer wire member each being independently slidable relative to one another to change the overall diameter, stiffness, and degree of pushability in advancement of the guidewire, without a need to exchange the guidewire or a portion thereof, and together the members function as a unitary structure such that a proximal region of said guidewire permits a medical device to be longitudinally advanced to a desired location in a patient.

19. The medical guidewire of claim 18, wherein the inner wire member has a locking member thereon movable by engagement with the intermediate wire member to a locking position to fix the position of the inner and intermediate wire members, and the intermediate wire member has a flared handle portion frictionally engageable with the outer member to fix the position of the outer and intermediate wire members.

* * * * *